(12) United States Patent
Spack et al.

(10) Patent No.: US 6,218,132 B1
(45) Date of Patent: *Apr. 17, 2001

(54) METHOD FOR MONITORING T CELL REACTIVITY

(75) Inventors: Edward G. Spack, Mountain View; Nancy G. Wehner, Fremont; Michael A. McCutcheon, Stanford, all of CA (US)

(73) Assignee: Anergen, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/977,650

(22) Filed: Nov. 24, 1997

Related U.S. Application Data

(63) Continuation-in-part of application No. PCT/US97/08699, filed on May 20, 1997, which is a continuation-in-part of application No. 08/657,939, filed on May 31, 1996, now Pat. No. 5,750,356.

(51) Int. Cl.$^7$ .......................... G01N 33/53; G01N 33/564

(52) U.S. Cl. ...................... 435/7.24; 435/7.94; 435/7.95; 436/506

(58) Field of Search .................................. 435/7.24, 7.94, 435/7.95, 372.3; 436/506

(56) References Cited

U.S. PATENT DOCUMENTS

| 5,128,270 | 7/1992 | Delacroix et al. . |
| 5,334,504 | 8/1994 | Wood et al. . |
| 5,344,755 | 9/1994 | Shearer et al. . |
| 5,750,356 | * 5/1998 | Spack et al. .................. 435/7.24 |

FOREIGN PATENT DOCUMENTS

WO 90/04182    4/1990   (WO) .

OTHER PUBLICATIONS

McCutcheon et al, Jour. Immunol. Meth; 210(2), 149–166, 1997.*

Czerkinsky, C. et al., "Reverse ELISPOT Assay For Clonal Analysis of Cytokine Production, I. Enumeration of Gamma–Interferon–Secreting Cells" *J. Immunol. Meth.*, 1988, vol. 110, pp. 29–36.

Link, H. et al., "Myasthenia Gravis: T and B Cell Reactivities to the β–Bungarotoxin Binding Protein Presynaptic Membrane Receptor" *J. Neuorological Sci.*, 1992, vol. 109, pp. 173–181.

Link et al. "The T–cell repertoire in myasthenia gravis involves multiple cholinergic receptor epitopes" *Scand. J. Immunol.*, 1992, vol. 36, pp. 405–414.

Lu et al. "Interferon γ–and interleukin–4–secreting cells in multiple sclerosis" *J. Neuroimmunol.*, 1993, vol. 46, pp. 123–128.

Lu et al. "Interleukin–2 secreting cells in multiple sclerosis and controls" *J. Neurol. Sci.*, 1993, vol. 120, pp. 99–106.

(List continued on next page.)

*Primary Examiner*—David Saunders
(74) *Attorney, Agent, or Firm*—Townsend and Townsend and Crew LLP

(57) ABSTRACT

This invention provides a highly sensitive assay for the detection of T-cells reactive to an antigen by detecting a soluble factor whose secretion is induced by stimulation of the T-cell by the antigen. The assay includes an antigen-driven proliferation of specific T cells prior to restimulation with irradiated antigen presenting cells (APCs) and antigen. In exemplary embodiments the assay is used to enhance the detection limits of human peripheral blood mononuclear cells (PBMCs) secreting interferon-γ (IFN-Y) and interleukin-2 (IL-2). The assay can be performed on previously frozen PBMCs, providing greater convenience in sample processing, multiple use of a single sample as an internal standard, and simultaneous analysis of samples collected at different time points.

32 Claims, 12 Drawing Sheets

OTHER PUBLICATIONS

Menz et al., "Analysis and sorting of live cells according to secreted molecules, relocated to a call–surface affinity matrix" *Proc. Natl. Acad. Sci. USA*, 1995, vol. 92, pp. 1921.

Olsson, T. et al., "Increased numbers of T cells recognizing multiple myelin basic protein epitopes in multiple sclerosis" *Eur. J. Immunol.*, 1992, vol. 22, pp. 1083–1087.

Olsson, T. et al., "Autoreactive T Lymphocytes in Multiple Sclerosis Determined by Antigen–Induced Secretion of Interferon–λ." *J. Clin. Invest*, 1990, vol. 86, pp. 981–985.

Plebanski et al., "In vivo primary responses of human T cells to soluble protein antigens" *J. Immunol. Meth.*, 1994, vol. 170, pp. 12.

Sharrock et al., "Limiting dilution analysis of human T cells: a useful clinical tool" *Immunol. Today*, 1990, vol. 11, pp. 281–286.

Söderström, M. et al., "Optic Neuritis and Multiple Sclerosis: The T Cell Repertoires to Myelin Proteins and MBP Peptides Change With Time" *Acta Neurological Scandinavica*, 1994, vol. 90, pp. 10–18.

Söderström, M. et al., "T Cells Recognizing Multiple Peptides of Myelin Basic Protein Are Found in Blood and Enriched in Cerebrospinal Fluid in Optic Neuritis and Multiple Sclerosis" *Scand. J. Immunol.*, vol. 37, pp. 355–368, 1993.

Sun, J.–B. et al., "T cells responses to human recombinant acetylcholine receptor–α subunit in myasthenia gravis and controls" *Eur. J. Immunol.*, 1992, vol. 22, pp. 1553–1559.

Weiner et al., "Double–blind pilot trial of oral tolerization with myelin antigens in multiple sclerosis" *Science*, 1993, vol. 259, pp. 1321.

\* cited by examiner

% POSITIVE RECALL ANTIGEN RESPONSES
IN RHEUMATOID ARTHRITIS PATIENTS

| 3 DAY ASSAY | | 10 DAY ASSAY | |
|---|---|---|---|
| TT | PPD | TT | PPD |
| 15.4% | 7.7% | 50.0% | 71.4% |

% POSITIVE ANTIGEN RESPONSES IN MS PATIENTS

| | 3 DAY ASSAY | | 10 DAY ASSAY | |
|---|---|---|---|---|
| | MBP | MBP 84-102 | MBP | MBP 84-102 |
| ALL MS PATIENTS | 28.0 | 20.0 | 36.0 | 48.0 |
| DR2+ MS PATIENTS | 33.3 | 13.3 | 40.0 | 40.0 |

METHOD FOR MONITORING T CELL REACTIVITY

CROSS REFERENCE TO RELATED APPLICATIONS

The present application is a continuation-in-part application of Patent Cooperation Treaty application No. PCT/US97/08699, filed May 20, 1997, which is a continuation-in-part of commonly assigned patent application U.S. Ser. No. 08/657,939, filed May 31, 1996 and now U.S. Pat. No. 5,750,356. Both of these applications are incorporated herein by reference in their entirety and for all purposes.

BACKGROUND OF THE INVENTION

This invention relates to detection of soluble factor secretion by activated T-cells. In particular, this invention relates to modifications of the standard ELISPOT assay.

Therapeutic strategies ranging from vaccine design to T cell specific immunosuppression require identification of immunodominant T cell epitopes and enumeration of T cell frequency. Several assays are currently employed to provide this information. Modified proliferation assays have been used to identify T cell epitopes based on stimulation indices of $\geq 2.0$ (Plebanski, M., and Burtles, S. S., *J. Immunol. Meth.* 170:15 (1994)), but this assay is extremely sensitive to variations in serum and often proves difficult for large scale clinical screenings. The limiting dilution assay (LDA) employs relatively large PBMC quantities and two rounds of in vitro stimulation to detect the T cell response to whole antigens or peptides (Sharrock, C. E. M. et al., *Immunol. Today* 11:281–286 (1990)). This assay has provided estimates of antigen specific CD4+ T cell frequencies ranging from approximately $1/10^3$–$1/10^5$ for alloreactive T cells (Sharrock supra) to $10^6$–$1/10^7$ for autoreactive T cells (Weiner, H. L. et al., *Science* 259:1321 (1993)). The LDA has been used to monitor efficacy in clinical trials, but the quantities of PBMC's (peripheral blood mononuclear cells) required limit the application of this assay in cases requiring frequent blood draws or the screening of large numbers of candidate peptides. Several flow cytometric methods can detect T cell activation by upregulation of characteristic markers such as CD69. Activation-induced T cell lymphokine production can be measured by flow cytometry using a monensin block of secretion, saponin permeabilization, and indirect immunofluorescent staining (Jung, T. et al., *J. Immunol. Meth.* 159:197 (1993)), or by trapping of secreted lymphokines on the surface of the secreting cell (Manz, R. et al., *Proc. Natl. Acad. Sci. USA* 92:1921 (1995)). These flow cytometry techniques are sufficiently sensitive when a relatively high frequency of T cells respond, as occurs in alloreactivity or superantigen stimulation, but they cannot detect most rare antigen-specific T cells. ELISA assays of lymphokine secretion are similarly limited to cases in which the responses of primed T cells, T cell clones, or high frequency T cells are measured. In situ hybridization of lymphokine mRNA is sufficiently sensitive to detect antigen-specific T cells with frequencies in the range of $1/10^4$–$1/10^5$ (Link, J. et al., *Neurol.* 44:728 (1994); Link, J. et al., *Ann. Neurol.* 35:197 (1994)), but this technique is not readily scalable to large sample numbers.

A modification of the ELISA assay (enzyme-linked immunosorbent assay), termed the immunospot or ELISPOT assay, has been developed to detect lymphokine secretion by individual T cells following antigen stimulation (Czerinsky, C., et al., *J. Immunol. Methods* 110:29–36 (1988); Olsson, T. et al., *J. Clin. Invest.* 86:981–985 (1990)). However, the sensitivity of the standard ELISPOT assay is low. For example, for many multiple sclerosis (MS) patients, the standard ELISPOT assay of T cell responses to autoantigens can only be detected in cells sampled from the CSF, which entails difficult sampling and low cell yield. Identifying peptide epitopes within autoantigens such as MBP (myelin basic protein) by this assay is even more difficult given the relatively low precursor frequency. Furthermore, counting ELISPOT sample wells under light microscopy is slow and somewhat subjective. It would be desirable to have improved methods of measuring lymphokine secretion by activated T-cells, particularly those which occur at low frequency. This invention fulfills this and related needs.

SUMMARY OF THE INVENTION

One aspect of the invention provides a method for detecting an antigen reactive T-cell in a biological sample suspected of containing said T-cells. The method comprises:

(a) stimulating the T-cells in the biological sample with the antigen for a first time period sufficient to permit T-cell expansion;

(b) restimulating the T-cells with an effective amount of a combination of the antigen and antigen presenting cells to induce secretion of a soluble factor;

(c) detecting the presence of the soluble factor by capturing the soluble factor on a solid support; and (d) relating the presence of the soluble factor on the solid support to the presence of the antigen reactive T-cell.

Optionally, a second soluble factor such as, for example, a cytokine(s) and/or growth factor(s) may be added to facilitate continued T-cell expansion. This second soluble factor may be the same or different to the soluble factor whose detection is related to the presence of the antigen reactive T-cell.

The methods disclosed herein can be used to detect rare T-cells, especially those reactive to autoantigens and occurring at low frequencies, as low as 1 T-cell per $10^5$ PBMCs. A related aspect of the invention uses frozen T-cells as an internal control to validate the assay.

Also provided are methods for:

(1) identifying an antigen which stimulates T-cells in a patient biological sample, (2) identifying a patient having T-cells reactive to an autoantigen, (3) screening for putative drugs capable of inducing deletion or unresponsiveness of T-cells, (4) the screening of potential blood donors for use in generating antigen specific clones, (5) the identification of T cell epitopes (6) monitoring of drugs/treatments which may induce a generalized state of immunosuppression, for safety or efficacy, and (7) monitoring of the immune response to antigen(s) over time.

BRIEF DESCRIPTION OF THE DRAWINGS

FIG. 4 shows assay results when PBMCs were isolated from the blood of an MS patient are treated with different antigens.

DETAILED DESCRIPTION OF THE INVENTION

Figure 1:
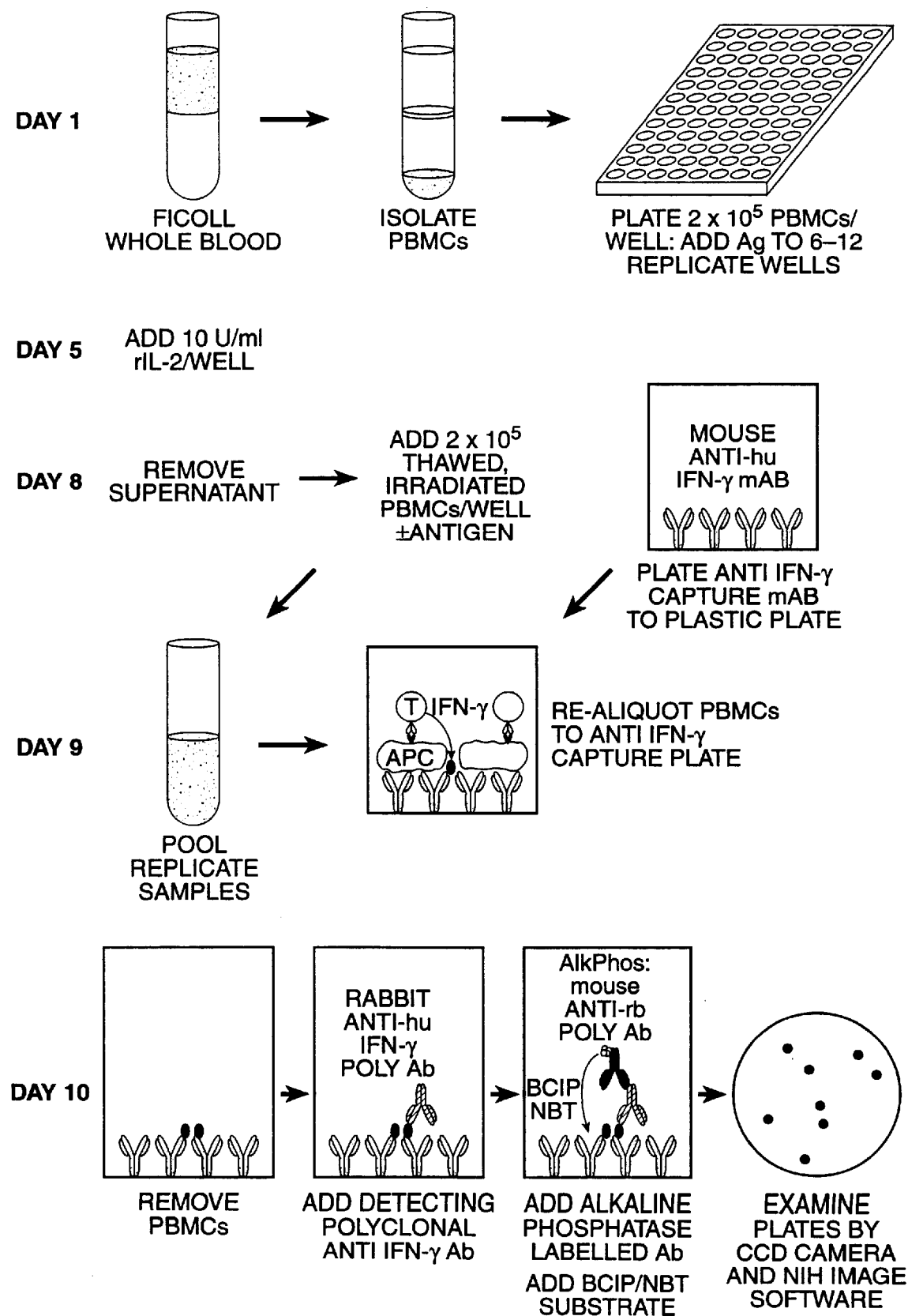
FIG. 1 shows a flow diagram illustrating the 10 day ELISPOT assay.

This invention relates to the detection of T-cells reactive to an antigen by detecting a soluble factor whose secretion is induced by stimulation of the T-cell by the antigen. In one aspect, this invention relates to an ELISPOT assay which expands the proportion of antigen-responsive T cells before detection of secretion of the soluble factor, providing sufficient sensitivity to permit the screening of T cells which are present at low frequency. As a result, rare T-cells, such as those which are reactive to an autoantigenic peptide can be detected and monitored with a higher level of confidence than previously possible. The assay is typically performed as a solid phase ELISA which produces a signal from each responding T-cell, thus allowing T-cell enumeration. In one embodiment, the signal is produced in the form of a chromogen precipitate from an enzyme label, (a "spot", hence the term ELISPOT), and if desired, the spots are quantitated with a video camera linked to analysis software. The software can objectively subtract nonspecific chromogen precipitation from total signal and rapidly quantitate the number of spots. These modifications facilitate the use of the ELISPOT assay as a high volume screen for T cell responses in applications from including epitope identification, tracking of a patient's autoantigenic reactivity over time, and assessment of therapeutic efficacy in clinical trials.

One aspect of the invention modifies the standard ELISPOT assay of lymphokine secretion by single cells to increase the sensitivity of the method. As described herein, the invention provides for the detection of antigen reactive T-cells which secrete a variety of soluble factors. These modifications include:

(1) a 7 day amplification of antigen responsive T cells prior to detection of a soluble factor, (2) addition of a second soluble factor (e.g., a cytokine(s) and/or growth factor(s)) to facilitate continued T-cell expansion, (3) restimulation of the T-cells to secrete additional soluble factor by adding a second round of antigen in conjunction with antigen presenting cells, and (4) using previously frozen PBMCs as an internal control.

The method of the present invention is referred to variously herein, including as an "ELISPOT" assay, a "10-day ELISPOT" assay," and as a "RECALL ELISPOT" assay, etc. The tradition ELISPOT assay is referred to herein as "standard" ELISPOT, "3-day" ELISPOT, "ELISPOT assay cited in the literature," etc.

An assay of such T cell reactivity has several applications:

1. Early detection of autoimmune disease.

2. Identification of important autoantigenic peptides in a patient subpopulation (e.g. a particular HLA-DR allele) and in an entire patient population, e.g., the identification of T cell epitopes.

3. Selection of patients with given T-cell reactivity for participation in clinical trials.

4. Monitoring patient T cell reactivity during the course of chronic-progressive and relapsing-remitting diseases. The pattern of T cell reactivity might be useful in predicting the onset of disease relapse before clinical symptoms worsen, aiding in the titration of a therapeutic regimen.

5. Measuring the efficacy of a therapeutic regimen

6. Screening for putative drugs capable of inducing deletion or unresponsiveness of T-cells or monitoring of drugs/ treatments which may induce a generalized state of immunosuppression, for safety or efficacy, and 7. Monitoring of the immune response to antigen(s) over time.

Thus, one aspect of the invention provides a method for detecting an antigen reactive T-cell in a biological sample suspected of containing said T-cells. The method comprises:

(a) stimulating the T-cells in the biological sample with the antigen for a time period sufficient to permit T-cell expansion, (b) restimulating the T-cells with an effective amount of a combination of the antigen and antigen presenting cells to induce secretion of a soluble factor, (c) detecting the presence of the soluble factor by capturing it on a solid support, and (d) relating the presence of the soluble factor to the presence of the T-cell.

Optionally, one may add a cytokine(s) and/or growth factor(s) to facilitate continued T-cell expansion during or after step (a).

The biological sample may be from any organism that produces T-cells, such as birds (e.g., chickens) or mammals (such as humans or non-human mammals). The biological sample may be a biological fluid such as, but not limited to, whole blood, serum, plasma, nasal secretions, sputum, urine, sweat, saliva, transdermal exudates, pharyngeal exudates, bronchoalveolar lavage, tracheal aspirations, cerebrospinal fluid, synovial fluid, fluid from joints, vitreous fluid, vaginal or urethral secretions, or the like. Herein, disaggregated cellular tissues such as, for example, hair, skin, synovial tissue, tissue biopsies and nail scrapings are also considered as biological samples.

The assay is particularly useful for assaying T-cells in blood samples. Blood samples are usually processed to remove erythrocytes and platelets (e.g., by Ficoll density centrifugation or other such methods known to one of skill in the art) and the remaining PBMC sample, which includes the T-cells of interest, as well as B-cells, macrophages and dendritic cells, is used directly in the assay.

T cell lines require large quantities of blood, often as much as a unit. Collection of such large quantities is often unsafe for patients with autoimmune disease. The assay described herein uses $4 \times 10^5$ PBMCs per well, i.e. $2 \times 10^5$ PBMCs for initial antigen stimulation and $2 \times 10^5$ irradiated PBMCs for restimulation. Therefore, several 15 ml blood collection tubes are generally sufficient for analysis of antigen reactivity with at least 6 wells per antigen.

The term "soluble factor" refers to proteins secreted by a T-cell in response to antigenic stimulation. A variety of secreted soluble factors can be detected by the assays disclosed herein. The soluble factors may be cytokines, lymphokines or chemokines. Typically this secreted factor is a lymphokine, such as enumerated below. As a result of the increased sensitivity of the assay, factors secreted by rare T-cells which occur in low frequency can be detected. Factors which are detected by this method include, but are not limited to lymphokines, cytokines and chemokines such as for example, IFN-γ, TNF-α, IL-2, IL-3, IL-4, IL-5, IL-10, IL-13, TGF-β, RANTES, and GM-CSF. As one of skill in the art will recognize, any secreted factor which has two epitopes, each of which can be recognized by the specific binding pair members used in the subsequent sandwich assay detection step can be detected by this assay. This method finds particular utility in detecting rare T-cells, such as those which are reactive to an autoantigenic peptide.

The term "cytokine" refers to proteins made by cells that effect the behavior of other cells. Cytokines made by lymphocytes are generally termed "lymphokines" or interleukins (abbreviated IL). The term "chemokines" refers to a subset of cytokines with low molecular weight which effect the migration and activation of cells. Cytokines include interleukins (e.g., IL-2, IL-3, IL-4, IL-5, IL-6, IL-10, IL-13 etc.,) macrophage arming factor, lymphocyte inhibition factor, macrophage inhibition factor, chemotactic factor, interferons, growth factors such as GM-CSF and the like.

The time period for T-cell expansion is typically greater than 3 days. Depending on the rapidity with which results are needed and the assay sensitivity required, this time period could be 5–7 days or as high as 10–14 days. With such long expansion phases it is generally advantageous to add a cytokine and/or growth factor at an intermediate point during the expansion phase to facilitate continued T-cell expansion and prevent premature cell death due to apoptosis.

The choice of cytokine and/or growth factor which is added to the assay medium to facilitate continued T-cell expansion is controlled partly by the subset of T-cells being detected. For example, IL-2 up-regulates expression of the IL-2 receptor and supports the expansion of $T_h1$ cells, whereas IL-4 supports the expansion of $T_h2$ cells. Thus, when the object of the assay is detection of a cytokine or cytokines secreted by $T_h2$ cells (e.g., IL-4, IL-5, and/or IL-10), the addition of IL-4 or another $T_h2$ cell-stimulating factor to facilitate $T_h2$ expansion will be advantageous.

When the object of the assay is detection of a cytokine or cytokines secreted by $T_h1$ cells (e.g., IFN-γ and/or IL-2), the addition of IL-2 or another $T_h1$ cell-stimulating factor (e.g., IL-12, or IL-2 plus IL-12) to facilitate $T_h1$ expansion will be preferred. In other cases, combinations of one or more cytokines and/or growth factors are used, and can be chosen to influence the type(s) of T cells expanded. Thus, for example, when expansion of both $T_h1$ cells and $T_h2$ cells is desired, a mixture of cytokines, such as IL-2 plus IL-4, may be used. The mixture of cytokines can be from a natural source or may be made by combining individual purified cytokines. One convenient source of a "cytokine mix" is the supernatant of mitogen stimulated T lymphocytes (e.g., phytohemagglutinin (PHA) -stimulated T lymphocytes; see, e.g., Alvarez et al. 1979, *J. Immunol.* 123:977). One exemplary cytokine mix is prepared by stimulating cultures of human PBMCs with 100 μg/ml of the mitogen phytohemagglutinin (PHA-P) and is available commercially (Human T-STIM; Collaborative Biomedical Products , Bedford, Mass.). Optionally, immunoaffinity chromatography is employed to remove the PHA before addition to T cells, which reduces nonspecific stimulation of the T cells.

In this modification of the standard ELISPOT assay, the number of progeny cells from a single precursor T-cell and consequently the amount of soluble factor-secreting cells increases. This leads to an increased number of "spots" on the solid surface being used and thus provides a greater assay response. Such an increased assay response is more amenable to statistical sampling and provides higher signal to background ratios, lower standard deviations and higher confidence levels. As a result, T-cells with expected frequencies in the range of 1 per $10^5$ PBMCs in the biological sample are detectable, frequently as low as 5 per $10^6$ PBMC's, often as low as 1 per $10^6$ PBMCs. Similar advantages accrue when a detection method other than an ELISPOT assay is used.

"Specific binding pair member" (sbp member) shall mean a molecule which is one of two different molecules, having an area on the surface or in a cavity which specifically binds to and is thereby defined as being complementary with a particular spatial and polar organization of the other molecule. The two molecules are related in the sense that their binding to each other is such that they are capable of distinguishing their binding partner from other assay constituents having similar characteristics. The members of the specific binding pair are referred to as ligand and receptor (antiligand), sbp member and sbp partner, and the like. Complementary sbp members bind to each other, as for example, a ligand and its complementary receptor. Sbp members will usually be members of an immunological binding pair such as an antigen-antibody, although other specific binding pairs, such as biotin-avidin, hormones-hormone receptors, nucleic acid duplexes, IgG-protein A, and the like are specific binding pairs which are not immunological binding pairs. In the context of this invention, specific immunological binding pairs include, but are not limited to, antibodies against secreted soluble factors, such as the lymphokines, cytokines and chemokines enumerated above, particularly anti-human antibodies and antibodies against specific epitopes of these secreted factors.

"Antibody" shall mean an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may include Fab, Fv and F(ab')$_2$, Fab', and the like.

It is typically advantageous to perform the stimulation/expansion phase described above on multiple duplicate samples and then pool the expanded samples prior to detection. This is particularly useful when assaying for rare T-cells of which only a few, e.g., as low as 1–2 T-cells/$10^5$ cells, sometimes as low as 5 T-cells/$10^6$ cells, may be present in the original sample. Pooling the samples before the detection step reduces sample to sample variation and increases the statistical confidence levels of the assay. Typically, the assay is run in triplicate or sextuplicate prior to pooling, though a different level of duplication can also be employed. It is generally desirable to perform the stimulation phases of the assay on plastic round bottom wells.

A variety of assay formats can be used to detect the increased levels of secreted factors produced by the assay described herein. Suitable assays include both solid phase (heterogeneous) and non-solid phase (homogeneous) protocols. The assays can be run using competitive or non-competitive formats, and using a wide variety of labels, such as radioisotopes, enzymes, fluorescers, chemiluminescers, spin labels, and the like. Such methods include, but are not limited to enzyme-linked immunosorbent assays (ELISA), both direct and reverse formats, and other solid phase assays. It will be recognized that negative controls, i.e., samples run without added antigen, and positive controls, i.e., samples run with antigens, such as tetanus toxoid, known to elicit lymphokine secretion from T-cells will be run as necessary under otherwise duplicative conditions to validate the assay results.

Some assays rely on heterogeneous protocols where a ligand complementary to the secreted factor (such as antibody against the secreted factor) is bound to a solid phase which is used to capture the secreted factor. The ligand may be conveniently immobilized on a variety of solid phases, such as dipsticks, particulates, microspheres, magnetic particles, test tubes, microtiter wells, and plastics, nitrocellulose or nylon membranes and the like, including polyvinyl difluoride (PVDF) (e.g., 96 well plate with a PVDF membrane base (Millipore MAIPS45-10))and ELISA grade plastic. The captured factor can then be detected using the non-competitive "sandwich" technique where a directly or indirectly labeled second ligand for the factor is exposed to the washed solid phase. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of secreted factors. Also see, "Enzyme immunohistochemistry" in *Practice and Theory of Enzyme Immunoassays,* P. Tijssen (Elsevier 1985).

A commonly used assay format is the antibody capture assay. The general protocol is simple: a ligand, e.g., an unlabeled antibody for the secreted factor, is immobilized on a solid phase, and the secreted factor is allowed to bind to the immobilized antibody. The bound secreted factor is then detected by using a labeled secondary reagent that will specifically bind to the captured factor ("direct sandwich assay"). Alternatively, the secondary reagent will not be labeled, but will be detected by subsequent binding to labeled tertiary binding reagent complementary to the second binding reagent ("indirect sandwich assay"). The strength of signal from the bound label allows the determination of the amount of secreted factor present in the sample and this in turn allows the quantitation of the number of activated T-cells present in the sample.

As noted supra, the sandwich assay can be used to detect any secreted factor which has two epitopes, each of which can be recognized by the specific binding pair members. Choosing appropriate capture and detection antibody pairs permits the application of this assay to the detection of T cells secreting a variety of soluble factors. A partial list of antibody pairs which can be used in this assay is presented in Table 1.

TABLE 1

| Lymphokine | Capture Antibody | Detection Antibody | Enzyme Link | Reference |
|---|---|---|---|---|
| IFN-α | b α-hIFN-α mAb (Wellcome Res Found) | m α-hIFN-α mAb (Copenhagen) | HRP-g α-migG (Jackson Labs) | 16 |
| IFN-γ | m α-hIFN-α mAb M700A (Endogen) | r α-hIFN-γ poly Ab P700 (Endogen) | m α-rabbit poly Ab: AlkPhos conj. | |
| | m α-hIFN-α mAb M700A (Endogen) | r α-hIFN-γ poly Ab P700 (Endogen) | bt-g α-rabbit IgG avidin-biotin-peroxidase | 19 |
| | m α-hIFN-α mAb M700A (Mabtech) | bt- m α-hIFN-γ mAb 7-B6 (Mabtech) | Avidin-AlkPhos | 1, 10, 17, 21 |
| | m α-hIFN-α mAb 7-B6 (Chromogenix AB) | bt- m α-hIFN-γ mAB 1-D1K (Chromogenix AB) | s-avidin- AlkPhos | 14 |
| | m α-hIFN-α mAb 7-B6-1 | bt- m α-hIFN-γ mAB 1-D1K (Bohringer Mannheim) | avidin-HRP (Sigma) | 2 |
| | m α-hIFN-α mAb 7-B6-5 | r α-hIFN-γ poly Ab (Inferon | bt-g α-rabbit poly Ab avidin- biotin- | 3, 4, 5, 6, 7, 8, 9, 12, 13 |

TABLE 1-continued

| Lymphokine | Capture Antibody | Detection Antibody | Enzyme Link | Reference |
|---|---|---|---|---|
| | m α-hIFN-α mAb 1598-00 (Genzyme) | Sciences) r α-hIFN-γ poly Ab IP-500 (Genzyme) | peroxidase (Vector Laboratories) bt-g α-rabbit poly Ab avidin-biotin-peroxidase | 11 |
| IL-2 | m α-hIL-2 mAb #202 (R&D Systems) | r α-hIL-2 poly Ab P600 (Endogen) | m α-rabbit poly Ab: AlkPhos conj. | 22 |
| IL-4 | * α-hIL-4 mAb IL4-1 (Mabtech) | bt.* α-hIL-4** IL4-2 (Mabtech) | avidin-AlkPhos | 17, 16 |
| | m α-hIL-4 mAb 82-4 (U. Stockholm) | bt-m α-hIL-4 mAb 12-1 (U. Stockholm) | avidin-AlkPhos | 10, 14 |
| | m α-hIL-4 mAb 1842-01 (Genzyme) | r α-hIL-4 poly BL-4B (Genzyme) | bt-g α-rabbit poly Ab avidin-biotin-peroxidase | 11, 15, 18 |
| IL-5 | rat anti-human EL-5 mAb M551 (Endogen) | biotinylated rabbit anti-human IL-5 polyclonal Ab M550B (Endogen) | neutravidin-AlkPhos (Pierce) | |
| IL-12 | *α-hIL-12 mAb 11.79.15 (Wistar) | bt-* α-hIL-12 mAb 8.6.2.1 (Wistar) | s-avidin-AlkPhos (Dianova) | 20 |
| TNF-α | m α-hTNF-α mAb clone 195 (Boehringer) | r α-hTNF-α poly Ab (Serotec) | bt-g α-rabbit IgG avidin-biotin-peroxidase | 19 |
| RANTES | m α-hRANTES mAb clone 21418.211 mAb 678 (R & D Systems) | biotinylated g-α-hRANTES (R & D Systems cat. no. BAF278) | s-avidin-AlkPhos (Dianova) | 22 |
| GM-CSF | m α-hGM-CSF ZM-213 (Genzyme) | r α-hGM-CSF LP-714 (Genzyme) | bt-g α-rabbit IgG avidin-biotin-peroxidase | 19 |

Abbreviations: b. bovine: g, goat: m. mouse: r, rabbit: α, anti.
References: i. Czerkinsky et al. J. Immunol. Methods 110:29–36, 1988; 2. Kabilan et al. Eur. J. Immunol. 20:1085–1089, 1990. 3. Olsson et al.. J. Clin. st. 86:981–985. 1990; 4. Link et al. J. Clin. Invest. 87:2191–2196, 1991. 5. Sun et al. J. Immunol.. 146:1490–1495, 1991; 6. Link et al. J. Neurol Sci. 109:173–181. 1992, 7. Link et al. Scand. J. Immunol. 36:405–414, 1992; 8. Olsson et al. Eur. J. Immunol. 22:1083–1087, 1992. 9. Sun et al. Eur. J. Immunol. 22:1553–1559. 1992. 10. ElGhazali et al. Eur. 1. Immunol. 23:2740–2745, 1993; 11. Lu et al. J. Neuroimmunol. 46:123–128, 1993; 12, Söderstrom et al. Scand. J. Immunol. 37:355–368, 1993, 13. Söderstrom et al. Acta Neurol. Scand. 90:10–18. 1994; 14. Surcel et al. Immunology 81:171–176, 1994; 15. Yi et al.. J. Neuroimmunol. 50:177–186, 1994; 16. Feldman et al. J. Leuk. Biol. 57:214–220, 1995; 17. Huang et al. Arterioscler. Thromb. Vasc. Biol. 15:1577–1583, 1995; 18. Yi et al. Blood 86:3043–3049, 1995; 19. Herr et al. J. Immunol. Methods 191:131–142, 1996; 20. Munk et al. Infect. Immun. 64:1078–1080. 1996; 21. Ronnelid & Klareskog J. Immunolo. Methods 200:17–26, 1997; 22. R & D Systems 1997 catalog (R & D Systems, Minneapolis, MN).

A variety of labeled secondary and/or tertiary reagents can be used to detect the presence of the bound secreted factor. Examples include, but are not limited to, anti-cytokine antibodies, anti-immunoglobulin antibodies, peroxidase/anti-peroxidase, avidin/biotin complexes, protein A and protein G.

Detectable labels suitable for use in the present invention include any composition detectable by photochemical, biochemical, immunochemical, electrical, optical or chemical means. Useful labels in the present invention include biotin for staining with labeled streptavidin conjugate, fluorescent dyes and/or substrates (e.g., fluorescein, Texas red, rhodamine, green fluorescent protein, ELF™ (Molecular Probes, Eugene, Oreg., catalog # E-6600), lissamine, phycoerythrin (Perkin Elmer Cetus), Cy2, Cy3, Cy3.5, Cy5, Cy5.5, Cy7, FluorX (Amersham) and the like (see, e.g., Kricka, 1992, Nonisotopic DNA Probe Techniques, Academic Press San Diego, Calif.)), radiolabels (e.g., $^3$H, $^{125}$I, $^{35}$S, $^{14}$C, or $^{32}$P), enzymes (e.g., horse radish peroxidase; alkaline phosphatase and others commonly used in an ELISA), calorimetric labels such as colloidal gold or colored glass or plastic (e.g., polystyrene, polypropylene, latex, etc.) beads and chemiluminscent labels. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent or chemiluminescent markers may be detected using a photodetector to detect emitted light. Enzymatic labels are typically detected by providing the enzyme with a substrate and detecting the reaction product produced by the action of the enzyme on the substrate, and colorimetric or fluorescent labels are detected by simply visualizing the colored label or fluorescent product. Labels which are particularly useful in an ELISPOT assay as described herein are those which can produce a particulate product, such as when the combination of an enzyme and a substrate which gives a precipitating product, which may be detected on the basis of, e.g., color or fluorescence. Combinations of such enzyme substrate pairs are alkaline phosphatase and 4-bromo-3-chloro indolyl phosphate/tetrazolium salts, napthol AS-MX or napthol AS phosphate/Fast Blue BBN or Fast Red TR; horse radish peroxidase and 4-chloro-1-naphthol, 3,3'-diaminobenzidine (DAB), p-phenylenediamine, 3-amino-9-ethylcarbazole (AEC), 5,5'-tetramethylbenzidine and the like; glucose oxidase, t-nitroblue tetrazolium chloride (t-NBT)/m-phenazine methosulfate, and alkaline phosphatase and ELF™-97 (Molecular Probes Cat. #E-6602).

It will be appreciated that, when more than one soluble factor is detected (e.g., using two or more detection antibodies), different labels may be chosen to distinguish between the secreted factors. In one illustrative example, a two color detection system is used in which a first detection antibody, e.g., an anti-IFN-γ detection antibody, is labeled (directly or indirectly, e.g., with secondary or tertiary reagents) with a first detectable label, such as rhodamine, and a second detection antibody, e.g., an anti-IL-10 detection antibody, is labeled with a second detectable label, such as fluorescein, that can be differentiated from the first label. The two or more soluble factors can be secreted by the same cell type (e.g., $T_h1$ cells) and/or may be secreted by two or more different cell types in a sample. Double labeling and detection techniques are well known in the art, and numerous variations in which combinations of detectable labels other than the rhodamine/fluorescein combination illustrated supra will be apparent to those of skill. See e.g., Harlow and Lane, ANTIBODIES: A LABORATORY MANUAL, Cold Spring Harbor, New York (1988) and Coligan et al. CURRENT PROTOCOLS IN IMMUNOLOGY 1997 ed. (John Wiley & Sons, N.Y. 1997, both of which are incorporated herein by reference in their entirety and for all purposes. For example, when fluorescently-labeled probes are used, it will be understood that pairs of fluorophores are chosen that have distinct emission patterns (wavelengths) so that they can be easily distinguished. Similarly, pairs of capture antibodies linked to different enzymes, e.g. alkaline phosphatase and horseradish peroxidase, which drive the precipitation of different colored substrates may be used. Numerous other variations and combinations will be apparent to those of skill.

In another aspect of the invention, a second round of stimulation is performed. Frequently, assays which are run with pooled samples as described above, and a second round of stimulation is done on the pooled samples. In one embodiment, this second round of stimulation is done with the patient's own cells. A portion of the patient sample is separately preserved, typically by freezing at the onset of the assay, often as low as at liquid nitrogen temperatures, and a remaining portion is expanded and pooled as described above. The preserved portion is thawed, treated by irradiation, chemical treatment (e.g. mitomycin C) or the like to block proliferative capacity and added to the expanded samples in conjunction with another round of antigen. This procedure serves to stimulate the T-cells with a second round of antigen presenting cells and the irradiation ensures that the added cells do not expand independently. Typically, this second round of stimulation is done for 1–3 days, preferably 1 day.

The antigen presenting cells (APCs) used in the assay may include B cells, macrophages, and/or dendritic cells, and/or other antigen-presenting cell types. In one embodiment of the invention, the APCs are introduced in a blood sample or in a PBMC sample prepared as described supra (i.e., containing a mixture of T cells, B cells, macrophages, dendritic cells in about the same relative proportions as in blood). In another embodiment, the T cells are stimulated by adding a single APC type, or cells enriched for one or more APC types. For example, dendritic cells (DCs) are especially proficient APCs, but are relatively rare in PBMC populations. Thus, a sample of APCs enriched for DCs may be used. Enrichment of specific APC types can carried out by art-recognized means such as purification (e.g., by methods well known in the art, e.g., florescence activated cell sorting [FACS], adhesion to specific surfaces [e.g., macrophage adhesion to plastic] and the like). In an alternative embodiment, one or more antigen presenting cell types is expanded in culture. For example, in one embodiment, dendritic cells are prepared from PBMCs by culture with granulocyte-macrophage colony stimulating factor (GM-CSF) (Sallusto et al., 1994, *J. Exp. Med.* 179:1109; Romani et al., 1994, *J. Exp. Med.* 180:83; Romani et al., 1996, *J. Immunol. Methods* 196:137; Bender et al., 1996, *J. Immunol. Methods* 196:121). Typically, the expansion of DCs is carried out by about 5 days to about 9 days in culture, typically about 7 days. Thus, it will be convenient to use a portion of PMBCs from a patient for stimulation with antigen on Day 1 of the assay, while another portion of PMBCs is cultured with GM-CSF (e.g., for 7 days) and used to stimulate the PMBCs containing the clonally-expanded antigen-specific T cells. Dendritic cells can also be obtained by in vitro culture of CD34+ peripheral blood mononuclear cells, for example with 50 ng/ml GM-CSF and 1,000 U/ml IL-4 induces differentiation to the DC lineage. Alternatively, DC lines can be established by culture of CD34+ cells with GM-CSF and TNF-α; however, cells grown under these conditions have a lower T cell stimulatory capacity than many APCs and are unable to present soluble antigens. It will be appreciated that other methods, or variations of the protocols supra, are also suitable to induce proliferation and differentiation of DC precursors in blood into cells that bear the surface markers and morphology of immature DCs. In one embodiment, the efficiency of antigen processing and presentation can be increased by incubation of antigen with specific antibodies and opsinization through the Fc receptor (FcR) on the DC.

Purified or enriched dendritic cells (or other APCs) can also be used for stimulation of T cells in the initial steps of the assay. For example, in one embodiment DCs from a patient are enriched or purified, combined with antigen, and added to a sample suspected of containing T cells (e.g., fresh or frozen PMBCs from the patient).

The antigen presenting cells used in this second round of stimulation may also come from a source other than the original patient, as long as one avoids a mismatching at some of the MHC class I or class II alleles which could result in a mixed lymphocyte reaction and unacceptably high background in the zero antigen negative control wells. For example, one can use lymphocyte cells transfected with the appropriate MHC II molecule involved in peptide binding and T-cell recognition. One may also use EBV (Epstein Barr Virus) transformed B-cells, either a homozygous cell line available commercially which matches the patient's MHC haplotype or a previously prepared EBV transformed B-cell line from the patient. Finally, one may perform this second round of stimulation with a MHC II-antigen complex which is immobilized on the surface of the well.

The simultaneous detection of more than one soluble factor in a sample has a variety of applications. For example, it is possible to detect and distinguish $T_h1$ cells and $T_h2$ cells in the same well by detecting soluble factors characteristic of each, providing information on the $T_h1/T_h2$ balance in the T cell response of patients and heathy donors. Examples of soluble factors characteristic of $T_h1$ cells include IFN-γ, IL-2 and TNF-β. Examples of soluble factors characteristic of $T_h2$ cells include IL-4, IL-5, IL-9 and IL-10. It will be appreciated that in the example of $T_h1$ and $T_h2$, or any other pair of different cell types, pairs of soluble factors are selected such that each is secreted or produced by one cell type, but not the other, under the conditions of the assay.

Determination of relative prevalence of cells secreting particular soluble factors is used in, e.g., diagnosis and prognosis of human diseases. For example, the relapse stage of multiple sclerosis (MS) is characterized by a relative increase in cells secreting $T_h1$ lymphokines, while increases in cells secreting $T_h2$ lymphokines occur during recovery stages. Monitoring these changes facilitates diagnosis and prognosis of MS and other chronic-progressive and relapsing-remitting diseases. It will be appreciated that differential detection of other combinations of secreted factors will be desirable; for example in diagnosis and treatment of Leishmania infection.

In one embodiment of the assay, a soluble factor secreted by a B cell (e.g., an immunoglobulin) is detected in the same well as the T cell soluble factor (e.g., at the same time). One reason the simultaneous detection of cytokine and antibody responses is useful is that many diseases involve pathological effects of both T cell products and B cell products. For example, MS involves both $T_h1$ cytokine responses (e.g., to myelin proteins) and antibody production (e.g., to myelin basic protein [MBP] and myelin oligodendrocyte glycoprotein [MOG]. By using the assay of the invention, it is possible to analyze the effects of various antigens on the production of anti-MBP and anti-MOG, antibodies which many believe are involved in the demyelination of nerves in MS.

To measure immunoglobulin secretion by individual B cells, antigen is plated onto the bottom of the ELISPOT plate. Typically, the plated antigen is the same as the antigen used to stimulate the T cells. In some cases, however, two or more different antigens are used. For example, a peptide component of myelin basic protein can be used as the T cell stimulatory antigen, and antibody reactivity to the full-length myelin basic protein measured. Similarly, a viral peptide can be used as the T cell stimulatory antigen and antibody reactivity to self-peptide measured. Other examples will be apparent to those of skill upon review of the present disclosure.

Secreted immunoglobulin with specificity for the plated antigen is immobilized by binding to the antigen, and is detected using an anti-species or anti-isotype (e.g., anti-IgG, IgM, IgE, IgD or IgA) detection antibody using routine methods (see, e.g., Harlow, supra; see also Czerkinsky et al., 1983, *J. Immunol. Methods* 65:109; Czerkinsky et al., 1988, *J. Immunol. Methods* 115:31; Quiding et al., 1991, *J. Clin. Invest.* 88:143; Sun et al, 1991, *J. Immunol.* 146:1490; Lu et al., 1993, *J. Neuroimmunol.* 43:145, each of which is incorporated herein in its entirety and for all purposes).

In one embodiment, the concurrence of secretion of a soluble factor by a T cell and an anti-antigen immunoglobulin by a B cell is determined. In this context, "concurrence" refers to secretion of soluble factor (e.g., cytokine) by a T cell that is in contact with, or close to (e.g., within less than about one, about two, or about five cell diameters), a B cell producing an anti-antigen immunoglobulin. It is well known that $T_h$ cells provide soluble and contact stimuli that influence the activation of B cells, leading to the secretion of immunoglobulin (Ig) whose isotype is influenced by the complement of cytokines secreted by the $T_h$ cell. Determination of $T_h1$ or $T_h2$ secretion and resulting immunoglobulin secretion would be useful information in tracking the development and treatment of many diseases.

In another embodiment, the assay is used to monitor the effect of certain therapeutics on the secretion of antibodies, such as antibodies implicated in autoimmune responses (e.g., anti-MBP and anti-MOG antibodies). For example, it has been reported that altered peptide ligands (APLs) may effect a beneficial switch in the T cell response from $T_h1$ to $T_h2$ cytokines (Brocke et al., 1996, *Nature* 379:343). The simultaneous measurement of T cell products (e.g., cytokines) and B cell products (e.g., specific antibodies) is used to demonstrate that increased secretion of such cytokines affects the level of specific antibodies (e.g., autoantibodies).

The methods disclosed herein can be used to detect T-cells reactive to a variety of antigens, including the autoantigens which are indicative of an autoimmune disease. Table 2 enumerates a representative and non-limiting selection of disease states and their implicated autoantigens.

TABLE 2

| DISEASE | KNOWN OR SUSPECTED AUTOANTIGENS |
| --- | --- |
| Multiple Sclerosis (MS) | myelin basic protein (MBP) |
| | proteolipid protein (PLP) |
| | major oligodendrocytic protein (MOG) |
| | myelin associated glycoprotein (MAG) |
| | αB-crystallin |
| Myasthenia Gravis (MG) | acetylcholine receptor (AChR) |
| Insulin Dependent Diabetes Mellitus (IDDM) | glutamic acid decarboxylase (GAD) insulin |
| Uveitis | S protein |
| Rheumatoid Arthritis (RA) | collagen |
| | heat shock proteins (HSPs) e.g. hsp65 |
| | aggrecans |
| | proteoglycans |
| | fillagrin |
| | link |
| Psoriasis | desmin |
| Pemphigus Vulgaris | epidermal cadherin |
| Inflammatory Bowel Disease (IBD) | tropomyosin |
| Systemic Lupus Erythematosus (SLE) | Sm, RNP histones |
| Graves Disease | thyroid stimulating hormone receptor |
| Hashimoto's Thyroiditis | thyroglobulin |
| | thyroid peroxidase |
| Goodpasture's Syndrome | collagen type IV |
| Autoimmune Thrombocytopenia Purpura | platelet integrin a IIb: IIIa |
| Autoimmune Hemolytic Anemia | Rh blood group 1 antigen |

Myelin basic protein and peptide components thereof are indicative of multiple sclerosis. Particular autoantigenic peptides which can be used in this assay are MBP 83-102 (this refers to the peptide composed of residues 83-102 of MBP) and MBP 144-163, the major oligodendrocyte glycoprotein peptides MOG 1-20 and MOG 41-60, and the proteolipid protein peptides PLP 40-60, PLP 89-106, PLP 105-124, PLP 30-49, PLP 95-116, and PLP 180-199.

Another aspect of the invention is a method of periodically monitoring levels of antigen reactive T-cells in a patient. This allows one to track the progression or amelioration of disease in a patient and also to track the efficacy of a therapeutic regimen. The method comprises:

(a) providing a sample of PBMCs from the patient;

(b) freezing a portion of the sample of PBMCs to provide a control sample;

(c) assaying the level of antigen reactive T-cells in the patient at periodic intervals using the assays described above;

(d) assaying the level of antigen reactive T-cells in a freshly thawed portion of the control sample using the assays described above; and (e) comparing the levels observed in (c) and (d) to monitor the levels of antigen reactive T-cells in the patient.

In one aspect, the method described above is useful for monitoring the effect of a drug or treatment on a patient by carrying out the RECALL ELISPOT before and after the treatment or treatments, and comparing the assay results.

As described in more detail in the Examples, the present invention has demonstrated that T-cells preserved, typically by freezing, can be thawed and assayed using the methods described herein without affecting the viability of the cells or the accuracy of the subsequent T-cell enumeration. Using these preserved T-cells as an ongoing control provides a baseline against which temporal fluctuations in a patient's T-cell level can be compared. Therefore, any observed variation in a patient's T-cell count can be normalized against this control and the residual variation, if any, can be attributed to the progression or amelioration of a particular disease state being monitored. Such studies can use T-cells which have been preserved for as long as six months, often as long as 1–2 years. An advantage of having such an external standard which provides a stable snapshot of the patient's initial condition is that low level variations in the assay can be attributed to an actual change in the patient condition. Apart from being an objective measure of the disease state, it also allows one to detect a change in disease state before more dramatic clinical symptoms appear.

The methods disclosed herein are also used to determine which patients react to a suspected or known autoantigen. This is useful for selecting patients for clinical trials in which one desires to test the efficacy of a particular drug for a disease state caused by a suspected or known autoantigen. It can also help determine the DR, DP or DQ restriction of this response by using blocking antibodies or transfected L cells as the antigen presenting cells.

Also provided are methods of determining/confirming whether an antigen, typically a protein or component thereof, is an autoantigen in a significant portion of a patient population. In some diseases, e.g., rheumatoid arthritis, there is no acknowledged dominant autoantigenic protein and the assays described herein can be used to compare T-cell responses of a patient sample to various whole proteins derived from inflamed joints. In other diseases, such as myasthenia gravis or multiple sclerosis, the autoantigen responsible for the disease is known or suspected, but the immunodominant portion(s) of the autoantigenic proteins which dominate the T-cell response are not known. In such situations, PBMCs can be stimulated with various peptides derived from the autoantigen, either using a complete set of overlapping peptides or a subset of only those peptides which bind strongly to the relevant MHC II allele. Alternatively, PBMCs can be stimulated with the entire autoantigen in the initial round of stimulation, and restimulated with suspected autoantigenic peptides. Such peptides can be prepared by solid phase peptide synthesis methods when their sequences are known or peptide fragments can be prepared from the autoantigen by chemical or enzymatic digestion, all methods known to one of skill in the art.

Also provided is a method for determining a T cell epitope. T cell epitopes are often identified by proliferation assay of short term lines or clones. The method of the invention is faster than establishing T cell lines or clones, requires less blood than traditional cloning, and provides cytokine profiles that in many cases are more informative than measurement of proliferation alone. Furthermore, to avoid artifacts that sometimes arise from peptide-driven cell lines (Matsuo et al., 1995), the assay described herein can be performed with an initial stimulation of whole antigen (e.g. myelin basic protein) or complex antigen mix (e.g. whole spinal cord homogenate) followed by restimulation on day 7 with peptide (e.g. MBP 84-102). Thus, the method of the invention is useful for identifying immunodominant epitopes in autoimmune diseases such as multiple sclerosis, diabetes, and rheumatoid arthritis.

Also provided is a method for obtaining T cell clones with particular antigen specificity by prescreening candidate donors using the method of the invention to identify samples with relatively high precursor frequencies to ensure better cloning success. In addition, the assay offers a rapid screening to qualify patients for inclusion in clinical trials of antigen specific therapies this.

The present invention also provides an assay useful for determining the stability of dominant immune responses and the extent to which epitope spreading occurs in normal and autoimmune reactivity. Moreover, because multiple lymphokine responses can be sensitively assayed, the role of $T_h1/T_h2$ cytokine profiles in disease onset, relapse, remission, and treatment can also be determined.

The present invention also provides an assay useful for monitoring levels of antigen reactive T-cells in a patient by (a) collecting and freezing samples of PBMCs from the patient at least two different times; and (b) thawing the samples and assaying the level of antigen reactive T-cells in the samples using the assay described herein. In some cases it will be desirable to carry out this monitoring when a drug or treatment is administered to the patient between the two collections of step (a).

Similarly, the effect of a drug or treatment on levels of antigen reactive T-cells in a patient may be determined by (a) assaying the level of antigen reactive T-cells in the patient at least one time using the assay described herein; (b) administering the drug or treatment to the patient; (c) reassaying the level of antigen reactive T-cells in the patient at least once after the administration of the drug or treatment; and (d) comparing the levels observed in steps (a) and (c) to determine the effect of the drug or treatment on levels of antigen reactive T-cells in the patient. This method will be useful to determine properties of a drug or treatment such as side effects (e.g., immunosuppression) or efficacy (e.g., when the drug/treatment is generally or specifically immunosuppressive or suspected of being generally or specifically immunosuppressive)

The invention also provides a method for identifying a T cell epitope (e.g., an immunodominant epitope) associated with a disease (e.g., an autoimmune disease) or symptom by, e.g., (a) determining the reactivity to an antigen of T cells from a first plurality of individuals, wherein said individuals are diagnosed with a the disease or symptom; (b) determining the reactivity to an antigen of T cells from a second plurality of individuals, wherein said individuals are not diagnosed with the disease or symptom; (c) comparing the reactivity of T cells from the first plurality of individuals to the reactivity of T cells from the second plurality of individuals; and, (d) correlating an increased level of reactivity to the antigen in first plurality of individuals compared to the second plurality of individuals with the presence in the antigen of a T cell eptiope associated with the disease or symptom. According to the method, the determination of the reactivity to the antigen in steps (a) and (b) is carried out using the RECALL ELISPOT assay disclosed herein.

In yet another aspect, the invention is related to the discovery that 3 day ELISPOT and 10-day ELISPOT (RECALL ELISPOT) responses from frozen cells were better than or equivalent to those obtained from fresh cells. Without intending to be bound by any particular mechanism, it is believed that this result is due to the elimination of inhibitory cryosensitive cells, possibly including platelets. Thus the invention provides a method for improving the background to signal ratio in an ELISPOT assay (e.g., a standard ("3-day") ELISPOT assay or the RECALL or 10-day ELISPOT assay) by freezing and thawing an antigen reactive T-cell in a biological sample at least once prior to stimulating the T-cells with an antigen in vitro. As used in this context, a response is "better" or "improved" when the ratio of background to signal is lower (i.e., less background) than the same assay carried out using fresh (i.e., never frozen) cells. "Background" is the number of "spots," or their equivalent, that result when the T cells in the biological sample are not stimulated with antigen (e.g., when a media control is used). "Signal" is the number of "spots," or their equivalent, that result when the T cells in the biological sample are stimulated with an antigen (e.g., comprising a T cell epitope).

Various aspects of the invention will now be illustrated by a description of experiments carried out.

EXAMPLES

EXPERIMENTAL METHODS

Antigens

The following antigens were tested for their ability to induce IFN-γ secretion by PBMCs: tetanus toxoid (TT) (List Biologicals #191B, Campbell, Calif.), tuberculin purified protein derivative from *Mycobacterium tuberculosis* (PPD) (Connaught #SP0008, Swiftwater, Pa.), and human myelin basic protein (hMBP) (Chemicon International, Inc. #AG42P, Temecula, Calif.). Peptides including the immunodominant peptides MBP 84-102 and MBP 143-168 were synthesized using F-MOC chemistry and checked for purity by HPLC and mass spectroscopy.

PBMC and Sera Collection

Blood and sera samples were obtained from healthy volunteers and from multiple sclerosis patients (Multiple Sclerosis Unit, Sinai Hospital, University of California at San Francisco) under an approved IRB protocol. Whole blood was collected in one unit containers or in three or four 15 ml heparinized VacutainerH tubes (Becton Dickinson #6489, San Jose, Calif.) and used within 24 hours of collection. PBMCs were purified by density centrifugation (450×g for 30 minutes) on Ficoll (Pharmacia LKB, Ippsala, Sweden), isolated from the gradient interface, washed twice in Dulbecco's phosphate buffered saline (DPBS, BioWhittaker #17-512Q, Walkersville, Md.), and resuspended in human T cell medium (hTCM): Eagles medium (αMEM, BioWhittaker #17-60SE), 5% heat inactivated human AB serum (Ultra Serum, Gemini Bio-Products Inc. #100-118, Calabasas, Calif.), 4 mM 1-glutamine (Bio-Whittaker #17-602E), 20 mM Hepes buffer pH 7.2 (Bio-Whittaker #17-737E), 100 U/ml penicillin, 100 μg/ml streptomycin sulfate (Bio-Whittaker #17-602E), and $5 \times 10^{-5}$ M 2-β-mercaptoethanol (Sigma Chemical Co. #M7522, St. Louis, Mo.). Sixty percent of the PBMCs were resuspended in freezing medium [10% dimethyl sulfoxide (Sigma Chemical Co.), 90% heat inactivated human AB serum (Gemini Bioproducts Inc. #100-112)] to a concentration of $5 \times 10^6$ cells/ml, frozen in a programmable liquid nitrogen freezer (Cryo-Med #990-C, New Baltimore, Mich.), and stored under liquid nitrogen until needed as antigen presenting cells (APCs).

Antigen Stimulation of PBMCs

The basic 10 day RECALL ELISPOT assay is summarized in FIG. 1. This summary describes the detection of IFN-γ, although, as discussed supra other factors may be detected. On day one of the assay, PBMCs at a concentration of $2 \times 10^6$ cells/ml were aliquotted at 100 μl/well into round bottomed sterile microtiter culture plates (Costar #3799, Cambridge, Mass.). A 10 μl volume of antigen at 100 μg/ml (whole MBP or MBP peptides) or at 50 μg/ml (tetanus toxoid or PPD) is added to triplicate or sextuplet sets of wells and the plate was incubated in a 5% $CO_2$ incubator. On day five, 10 μl/well of 100 U/ml stock recombinant IL-2 (Advanced Biotechnologies Inc.) was added to each well. On day 8, frozen PBMCs were thawed, washed in cold hTCM, resuspended to a concentration of $4 \times 10^6$ cells/ml in warm hTCM, and γ-irradiated (3000 RADS). Fifty microliters of supernatant was removed from each microtiter well and replaced with 50 μl of irradiated PBMCs and 10 μl of the appropriate 10× antigen stock.

Capture and Detection of IFN-γ Secreted by Individual Antigen-Stimulated Cells Lymphokine secretion by individual antigen-stimulated T cells was assayed by a modification of the standard ELISPOT protocol. The lymphokine capture plate was prepared one day in advance, on assay day 8. IFN-γ capture antibody (monoclonal mouse anti-human IFN-γ, Endocen #M700A, Cambridge, Mass.) diluted to 10 μg/ml in sterile 0.1 M $NaHCO_3$ pH 8.2 buffer was aliquotted at 50 μl/well in flat bottomed 96 well sterile microtiter plates (Comina, #25801) and incubated at 4° C. for 24 hours. Prior to use, excess antibody was removed and wells were washed twice with DPBS. To block further nonspecific protein binding, plates were incubated with 250 μl/well of PBS+5% BSA at room temperature for 1 hour. After discarding the blocking solution, wells were washed twice with PBS, followed by hTCM in preparation for the antigen stimulated cells. Twenty-four hours after the second antigen stimulation (assay day 9), the stimulation plate was spun for 5 minutes at 1200 RPM in a Beckman CS-6R centrifuge and 90 μl of supernatant was carefully removed from each well with a micropipette. The pelleted cells were resuspended in 100 μl of hTCM, replicates pooled in sterile tubes (Costar cluster tube #4411), transferred to the prepared anti-IFN-γ capture plate, and incubated undisturbed at 37° C. for 20 hours. At the end of the IFN-γ secretion phase (assay day 10), the cells were discarded and the plates were hand washed three times with PBS+0.1 Tween-20 (PBST). A final aliquot of PBST was added to the wells and allowed to stand for ten minutes, removed, and the wells were washed three times with PBST in an Ultrawash Plus plate washer (Dynatech Laboratories, Chantilly, Va.). A 100 μl aliquot of rabbit anti-human IFN-γ polyclonal antibody (Endogen #P-700) diluted 1:500 in PBST+1% BSA was added to each well for 2.5 hours at room temperature with gentle rocking. Unbound anti-IFN-γ polyclonal antibody was removed by three washes with PBST in an automated plate washer, followed by a wash with 250 μl of 1× Tris-buffered saline+0.05% Tween 20 (TBST). Next, a 100 μl aliquot of 1:2500 alkaline phosphatase-conjugated mouse anti-rabbit polyclonal antibody diluted in TBST+1% BSA was added to each well and incubated at room temperature for 1.5 hours with gentle rocking. Alkaline phosphatase substrate solution (APSS) was prepared immediately before use by mixing 32 μl of p-Toluidine salt (BCIP, GIBCO-BRL #19290-016, Grand island, N.Y.) and 44 μl nitroblue tetrazolium chloride (NBT, GIBCO-BRL #18280-016), Grand Island, N.Y.) and 44 μl nitroblue tetrazolium chloride (NBT, GIBCO-BRL #18280-016) with 10 ml alkaline phosphatase buffer (APB=0.1 M NaCl, 0.05 M MgCl2, 0.1 M Tris HCl, pH 9.5) and passing through a 0.22 μM filter. Prior to addition of the APSS, excess enzyme-conjugated antibody was removed by three washes with TBST and one wash with APB. To develop, 50 μl of APSS was added to each capture well and the reaction was incubated with gentle rocking at room temperature until color reaction was visible (generally within 5–45 minutes). To stop the colorometric reaction, plates were washed three times in dH$_2$O in an automated plate washer, inverted to minimize deposition of dust in the wells, and dried overnight in the dark at 28° C. in a dust free drying oven.

Capture and Detection of IL-2 Secreted by Individual Antigen-Stimulated T Cells

A similar method was followed for the assessment of IL-2 secretion, with the modifications of a different lymphokine capture matrix (PVDF plate) and a shorter incubation period after the re-stimulation of the PBMCs. The lymphokine capture phase was performed in a 96 well plate with a PVDF membrane base (Millipore MAIPS45-10). Plates were prepared for IL-2 capture on assay day 7 by prewetting with ethanol, washing with NaHCO$_3$ binding buffer, and incubating with anti-IL-2 capture antibody (R&D Systems MAB202) at a concentration of 10 μg/ml in NaHCO$_3$ binding buffer, at 4° C. overnight. At each washing step, solutions were removed by vacuum aspiration on a vacuum manifold (Millipore #MAVMO9601). On day 8, the IL-2 capture plates were blocked with 5% BSA in PBS for ≧2 hours at room temperature and washed with hTCM. Washing and restimulation of PBMCs with irradiated autologous APCs±antigen was performed as outlined above. However, the more rapid kinetics of IL-2 secretion require antigen restimulation of the PBMCs directly in the PVDF IL-2 capture plate. The re-simulated PBMCs in the IL-2 capture plate were incubated overnight at 37° C. On day 9 wells were washed 3 times in PBST, incubated in PBST for 10 minutes, and washed an additional three times in PBST. Care was taken to flush the membrane thoroughly and to remove all solution from the underside of the PVDF membrane. Next the anti-IL-2 detection antibody (Endogen #P-600, rabbit and human IL-2 polyclonal antibody) was added at a 1:500 dilution in PBS/1% BSA and incubated for 2.5 hours. Plates were then washed four times in TBST and alkaline phosphatase-conjugated mouse anti-rabbit polyclonal antibody at 1:2500 dilution in TBST was added for 1.5 hours. Following this incubation, plates were washed in TBST and APB as described in section 2.4 above, followed by the addition of BCIP/NBT substrate in APB and development of 2–30 minutes. Care was taken to avoid overdevelopment, which occurred more rapidly in PVDF membranes than in plastic plates and which led to a general purple background that could interfere with computerized image analysis.

Automated Quantitation of the ELISPOT Reaction by Video Capture Imaging and Computer-Assisted Analysis Spots in individual wells were counted by video capture and computer-assisted image analysis. Prior to counting, the bottom of each plate was cleaned with ethanol (for IL-2 the bottom of the plate is not wiped with ethanol) and dust was blown from each well with Dust-Off (Falcon Safety Products, Branchburg, N.J.). The dried plates were mounted on a customized lightbox with a ring illuminator (Leica #31-36-17-01) approximately 31 cm from a 0.75 cm diameter circular aperture. The image of individual wells was captured by a Cohu CCD video camera (LighTools Research, Encinitas, Calif.) connected to a LighTools frame integrator. The image was stored in a Macintosh (PowerMAC 7100/80) computer equipped with a video card (Scion LG3, Frederick, Md.) and the number of spots were quantitated using NIH Image 1.59 software (available at http://rsb.info.nih. gov/nih-image/ on the World Wide Web).

For each plate, positive and negative control wells were used to set the contrast and brightness via the "Look Up Table" (LUT) palette. Adjusting the contrast optimizes the resolution of the spots, and contrasting between the positive and negative plates ensured optimal signal-to-noise. Once set, this contrast setting was used for viewing only. Next, "Threshold" was selected from the options menu to convert the grayscale image to black and white. Thresholding was adjusted with the LUT to a point where the well edge was eroded. Using the wand tool, the thresholded image was outlined to subtract the edge of the well which, due to refraction and edge effects, caused problems for the quantitation software. The threshold option is not selected for IL-2 plates because the plates are illuminated from above and the wand tool is not used in the counting of the wells. Instead, a preset circle is used to encircle most of the well. The rest of the process is identical to the standard IFN-γ assay. The "density slice" function was then selected, specifying a "slice" of the grayscale spectrum for analysis. This enhances the resolution of spots over debris and nonspecific chromagen deposition. The image was converted to binary, eroded, and spot size limits were set under the "Analyze Particles" function. This size restriction eliminates small, nonspecific background spots, debris, and large false patches. In general, the spot size restrictions were set at a minimum of 12 and a maximum of 1,000 pixels. To speed and standardize the analysis, macros were written to set the parameters at empirically established optimal settings, which were maintained for each well in a 96-well plate.

Statistical Analysis

Counts from replicate wells are compiled on a Microsoft Excel spreadsheet and means and standard deviations were calculated. Mann-Whitney statistical analysis was employed to calculate the significance-of spot numbers observed in medium only negative control versus antigen-stimulated samples. A p value of ≦0.05 in comparison of antigen and medium control wells was defined as a positive antigen response.

Abbreviations

The following abbreviations are used herein: Ab—antibody; AP—alkaline phosphatase; APCs—antigen presenting cells; BCIP—5-bromo-4-chloro-3-indolyl phosphate; DPBS—Dulbecco's phosphate buffered saline; HIM—heat inactivated normal; MBP—myelin basic protein; ME—mercaptoethanol; MG—myasthenia gravis;

MS—multiple sclerosis; MAX.—methotrexate; NBT—nitroblue tetrazolium chloride; NIH—National Institute of Health; NSAIDs—non-steroidal anti-inflammatory drugs; PBMCs—peripheral blood mononuclear cells; RA—rheumatoid arthritis; PVDF-polyvinyl difluoride.

EXPERIMENT I

Measurement of Antigen Reactive T-Cells by IFN-γ Capture

Peripheral blood was diluted threefold in Dulbecco's phosphate buffered saline (DPBS), underlain with 15 ml of Ficoll (Pharmacia Ficoll-Paque #17-0840-02, Piscataway, N.J.) per 40 ml diluted blood in a 50 ml polypropylene centrifuge tube, and spun at 2000 RPM for 20 minutes in a Beckman CS-6R centrifuge (Beckman Inc., Palo Alto, Calif.). The buffy layer at the DPBS/Ficoll interface was removed, washed twice with DPBS and once with human tissue culture medium (hTCM: αMEM+5% heat inactivated human AB serum (Ultraserum, BioWhittaker, Walkersville, Md.), penicillin/streptomycin, 1-glutamine) at low RCF to remove platelets. Sixty percent of the PBMCs are resuspended in freezing medium (10% dimethyl sulfoxide(Sigma Chemical Co., St. Louis, Mo.), 90% fetal bovine serum to a concentration of $5 \times 10^6$ cells/ml, frozen in a programmable Cryo-Med (New Baltimore, Mich.) cell freezer, and stored under liquid nitrogen until needed.

The purified PBMCs were plated at $2 \times 10^5$ cells/well at a volume of 0.1 ml in 96 well Costar cell culture plates. An equal volume of antigen at 10 μg/ml was added to triplicate or sextuplet sets of wells and the plate was incubated in a 37° C., 5% $CO_2$ incubator. On day five, 10 μl/well of 100 U/ml stock recombinant IL-2 (Advanced Biotechnologies Inc., Columbia, Md.) was added to each well. On day 8, frozen PBMCs were thawed, washed in DPBS+0.5% bovine serum albumin (BSA) to remove DMSO, resuspended to a concentration of $4 \times 10^6$ cells/ml in hTCM, and γ-irradiated (3,000 RADS). Fifty microliters/well were dispensed along with 50 μl of the appropriate antigen at a stock concentration of 40 μl/ml to give a final antigen concentration of 10 μg/ml.

To prepare a capture plate, IFN-γ capture antibody (monoclonal mouse anti-human IFN-γ, Endogen #M700A, Cambridge, Mass.) was diluted to 10 μg/ml in sterile 0.1 M $Na(CO_3)_2$ pH 8.2 buffer, aliquotted at 50 μl/well in flat bottomed 96 well sterile microtiter plates (Corning Costar Corp.), and incubated at 4° C. for a minimum of 24 hours. Prior to use, excess antibody was removed and wells are washed twice with dPBS+1% Tween 20 (PBST). To block further nonspecific protein binding, plates are incubated with 250 μl/well of PBS +5% BSA at room temperature for 1 hour. After discarding the blocking solution, wells were washed once with PBST (0.1% Tween), followed by hTCM in preparation for the antigen stimulated cells.

On day 9 of the assay, twenty four hours after the second antigen stimulation, the stimulation plate was spun for 5 minutes at 1500 RPM in a Beckman CS-6R centrifuge and 90 μl of supernatant was carefully removed from each well with a micropipette. The pelleted cells were resuspended in 100 μl of hTCM, pooled in sterile tubes (Corning Costar corp sterile ClusterTAb #4411, Cambridge, Mass.), mixed and transferred into an equal number of wells of an anti IFN-γ capture plate. Capture plates are incubated undisturbed at 37° C. for 16–20 hours. At the end of the IFN-γ secretion phase, the cells were discarded and the plates are washed three times with 0.1% PBST. A final aliquot of PBST was added to the wells for ten minutes, removed, and 100 μl of a 1:500 dilution of rabbit anti-human IFN-γ polyclonal antibody (Endogen #P700, Cambridge, Mass.) in PBST+1% BSA was added to each well for 3.5 hours at room temperature with gentle rocking. Unbound anti-IFN-γ polyclonal antibody was removed by three washes with PBST, followed by a wash with 250 μl of 1× Tris-buffered saline+0.05% Tween 20 (TBST). Next, a 100 μl aliquot of 1:5000 alkaline phosphatase-conjugated mouse anti-rabbit polyclonal antibody (Jackson Immunological #211-055-109, West Grove, Pa.) diluted in TBST was added to each well and incubated at room temperature for 1.5–2 hours with gentle rocking. Excess enzyme-conjugated antibody is removed by three washes with PBST and two washes with alkaline phosphatase buffer (APB=0.1 M NaCl, 0.05 M $MgCl_2$, 0.1 M Tris HCl, pH 9.5) followed by addition of the substrate mix of p-Toluidine salt and nitroblue tetrazolium chloride (BCIP/NBT, GIBCO BRL #18280-016, Gaithersburg, Md.). To stop the calorimetric reaction, plates were washed three times in $dH_2O$, inverted to minimize deposition of dust in the wells, and dried overnight at 28° C. in a dust free drying oven.

Images of the spots corresponding to the lymphokine secreted by individual antigen-stimulated T cells are captured with a CCD video camera and the image is analyzed by NIH image software. Captured images are enhanced using the Look Up Table which contrasts the images. Thresholding is then applied to every image and a wand tool is used to highlight the border to effectively subtract the edge of the well so that background counts won't be high and artificial. Density slicing over a narrow range is then used to highlight the spots produced from secreting cells. Pixel limits are set to subtract out small debris and large particles, and the number of spots falling within the prescribed pixel range are counted by the software program. Totals from each well are then manually recorded for future analysis. Alternatively, spots can be counted by other commercially available or customized software applications, or may be quantitated manually by a technician using standard light microscopy. Spots can also be counted manually under a light microscope.

Figure 2:
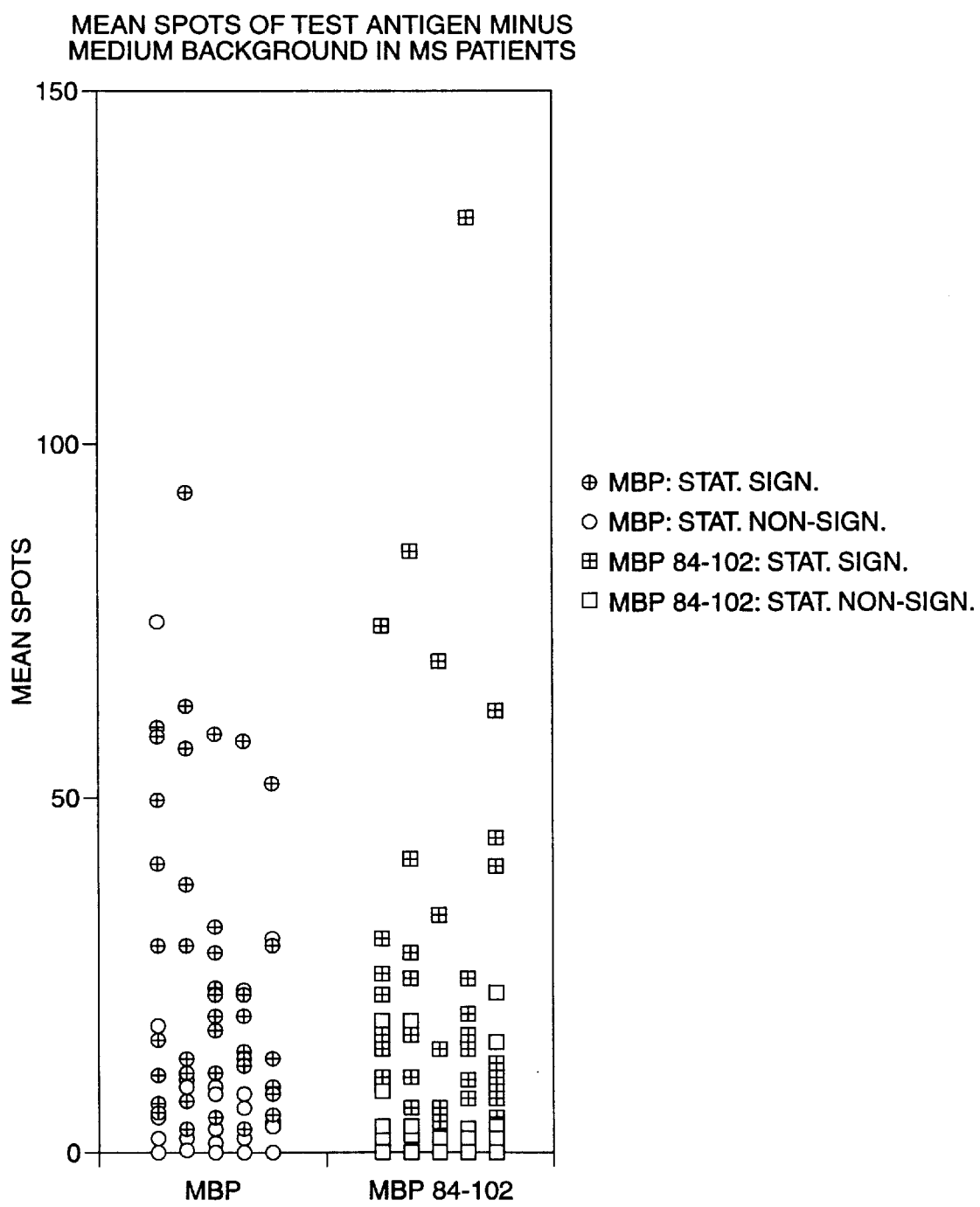
FIG. 2 shows MBP and MBP 84-102 reactivity in PBMCs from MS patients.
Figure 3:
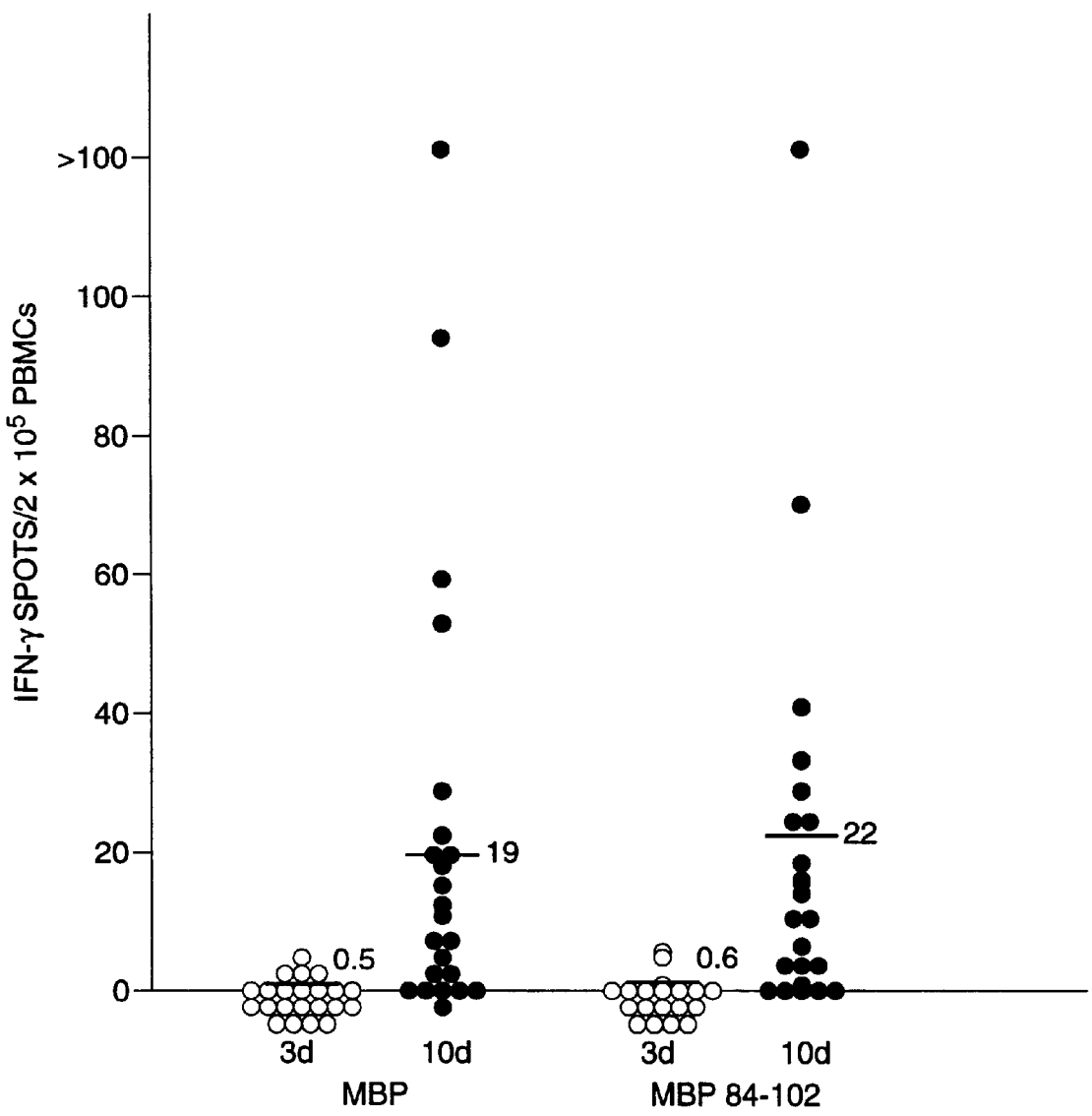
FIG. 3 shows the comparison of ELISPOT responses to MBP and MBP 84-102 in the 3 day and 10 day ELISPOT format.

FIG. 2 shows measurements of the reactivity of MS patients and healthy donors to MBP and MBP 84-102 using the above described assay. FIG. 3 shows the comparison of ELISPOT responses to MBP and MBP 84-102 in the 3 day and 10 day ELISPOT format. A total of 50 MS patients were tested for IFN-γ response to whole myelin basic protein (MBP) and to the immunodominant MBP peptide, MBP 84-102. Twenty-five of the patients were screened with the 3 day assay, and in agreement with published reports the level of response over background was very low. In contrast, a substantial percentage of the 25 patients screened by the 10 day ELISPOT showed a statistically significant response to whole MBP and/or to MBP 84-102, with an average of 19 spot forming cells (SFCs )/$2 \times 10^5$ PBMCs in response to MBP and 22 SFCs/$2 \times 10^5$ PBMCs in response to MBP 84-102. Each data point represents the average response of sextuplet samples from an individual, with the average response to medium subtracted. The means of each set of patients is indicated by a bar.

Spots generated in the standard ELISPOT assay are counted in most laboratories under magnification by a dissection microscope. Variations in the size of spots can hamper the objective enumeration of these spots. To accommodate higher throughput and provide greater consistency images of each well were recorded with a CCD video camera and quantitated the spots with NIH Image analysis software. To quantitate the spots, a circle 400 pixels in diameter is placed over the area to be counted. The density slice function selects the grayscale range for analysis, and after conversion to binary the spots within the set size limits are quantitated. The lower size limit is set empirically using the negative control plate to subtract out very small debris (generally<12 pixels) and the upper limit is set to ignore large clumps (generally>1,000 pixels). The density and size settings are constant for the analysis of an entire experiment.

Figure 4A:
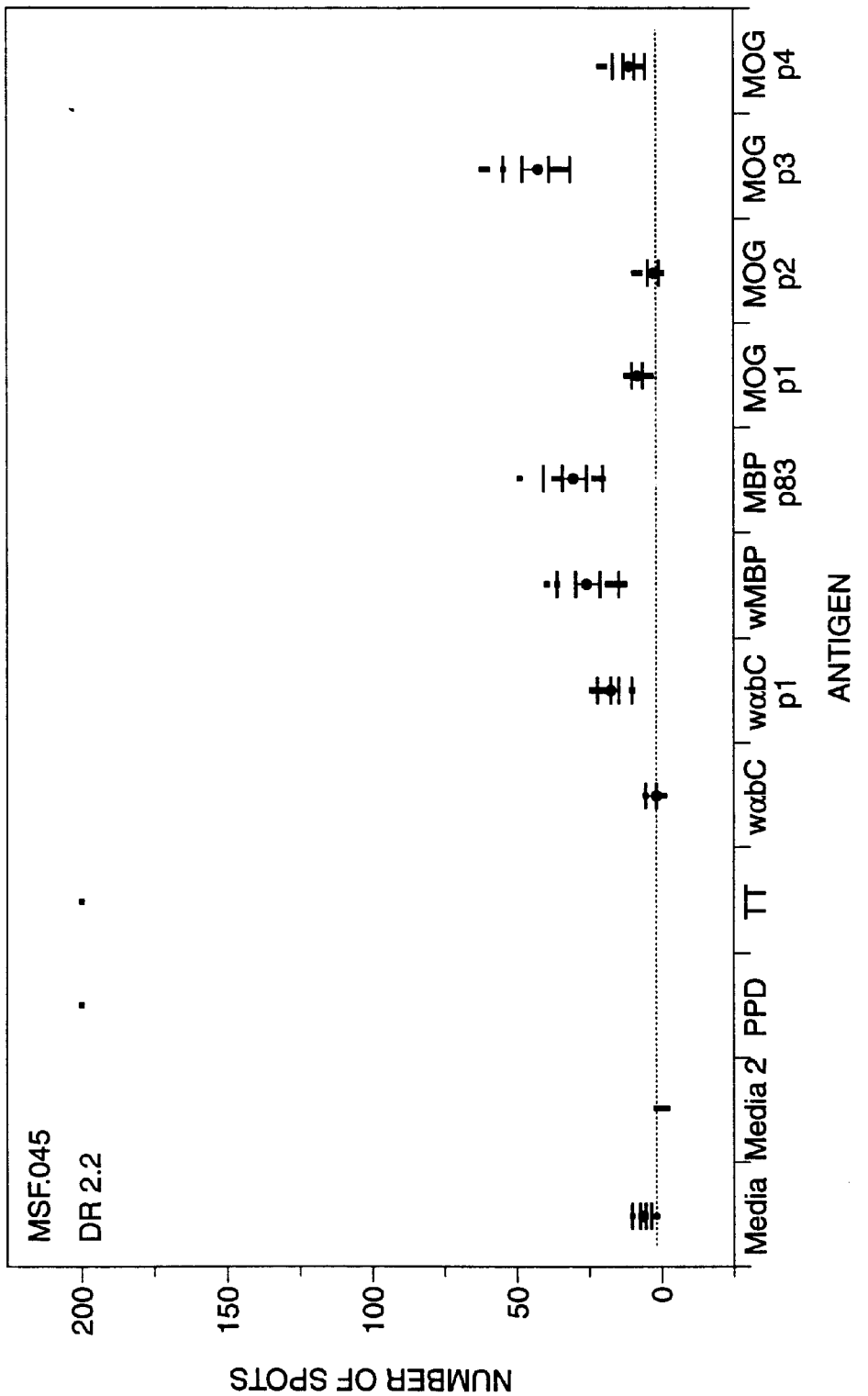
FIG. 4A: Distribution of spot numbers in sextuplet samples, including mean (large bar) and standard deviation (short bars). The data is analyzed and plotted by the JUMP program.
Figure 4B:
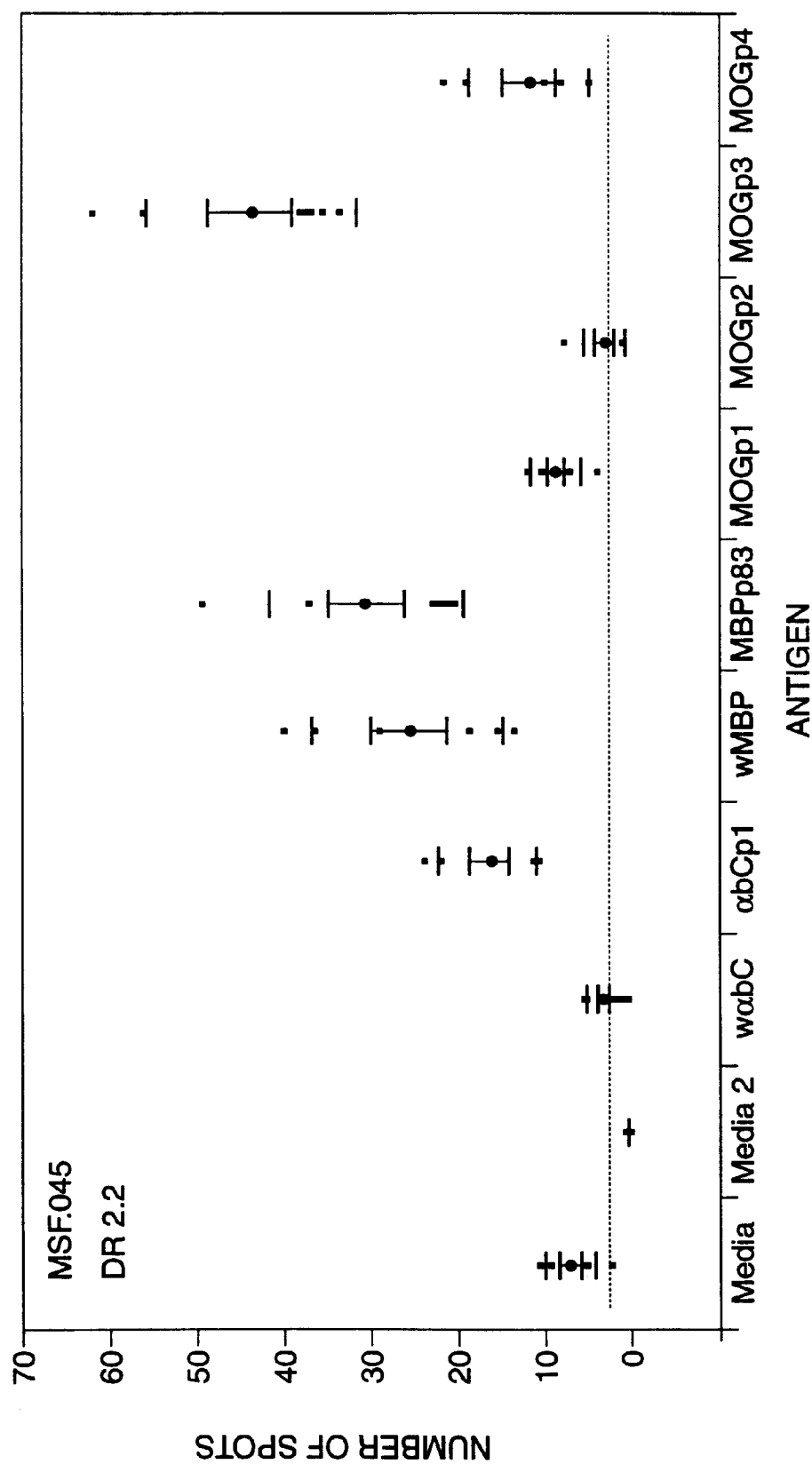
FIG. 4B: Data from FIG. 4A without TT and PPD responses, plotted on an expanded scale to show the level of replicate sample deviation.

FIG. 4 shows an example of the standard deviations, means, and distribution of spots for several sextuplet sets of wells treated with different antigens. PBMCs were isolated from the blood of an MS patient and stimulated in a 10 day assay and were tested for IFN-γ secretion in response to medium, positive control antigens (purified protein derivative of M. tuberculosis, PPD; tetanus toxin, TT), myelin protein antigens (αB-crystallin, αBC; myelin basic protein, MBP; myelin oligodendrocyte glycoprotein, MOG), or potentially immunodominant myelin protein peptides (αBCpl from αB-crystallin, MBPp83 from myelin basic protein, and MOG peptides p1-4 from myelin oligodendrocyte glycoprotein). Frequently in this recall assay the higher frequency responder T cells expand beyond the capacity of the assay to resolve individual spots. For example, in FIG. 4A the IFN-γ response to TT and PPD is >200 spots, too numerous to count accurately. Several myelin antigens provoked a smaller but statistically significant response, which is seen better in the expanded plot of FIG. 4B. The number of spots produced by media alone is low and consistent in two sextuplet sets. Several myelin antigens do not induce responses above this background, but several other antigens or peptides induce statistically significant increases in spot numbers (e.g., MBPpl and MOGp3). The low standard deviation among replicate wells is demonstrated by the distribution of totals for each of the six wells in a set and by the bars. This consistency is aided by the pooling of samples before capture, and is a critical point in determining which responses are statistically significant.

EXPERIMENT II

Measurement of Antigen Reactive T-Cells by IL-2 Capture

The ELISPOT assay was carried out as described supra in the methods section. Compared to IFN-γ, the more rapid induction and secretion of IL-2 required pooling and transfer of cells within 2 hours after stimulation. For the detection of IL-2, PVDF membranes were more sensitive and gave a better signal:noise ratio than ELISA grade plastic. (The PVDF also allowed detection of low frequency IFN-γ responses, but at higher levels of responding cells some background problems were encountered.) Typically IFN-γ 10-day ELISPOTs are carried out using plastic and IL-2 10-day ELISPOTs use PVDF.

Figure 5A:
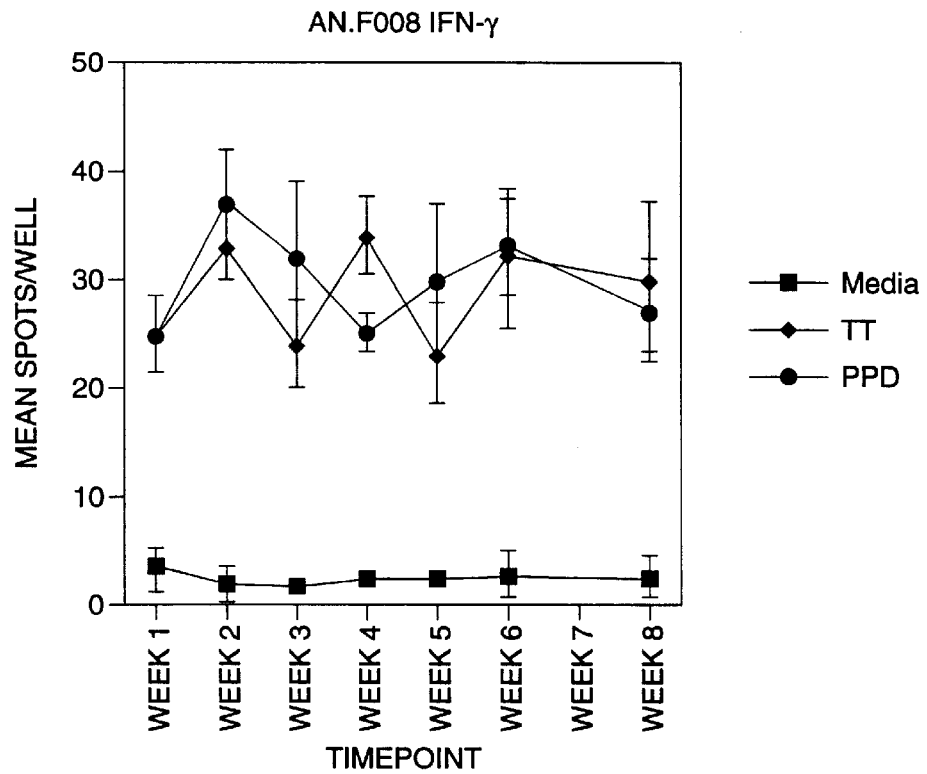
FIGS. 5A and 5B show T cell reactivity over time measured using INF-γ and IL-2 capture.
Figure 5B:
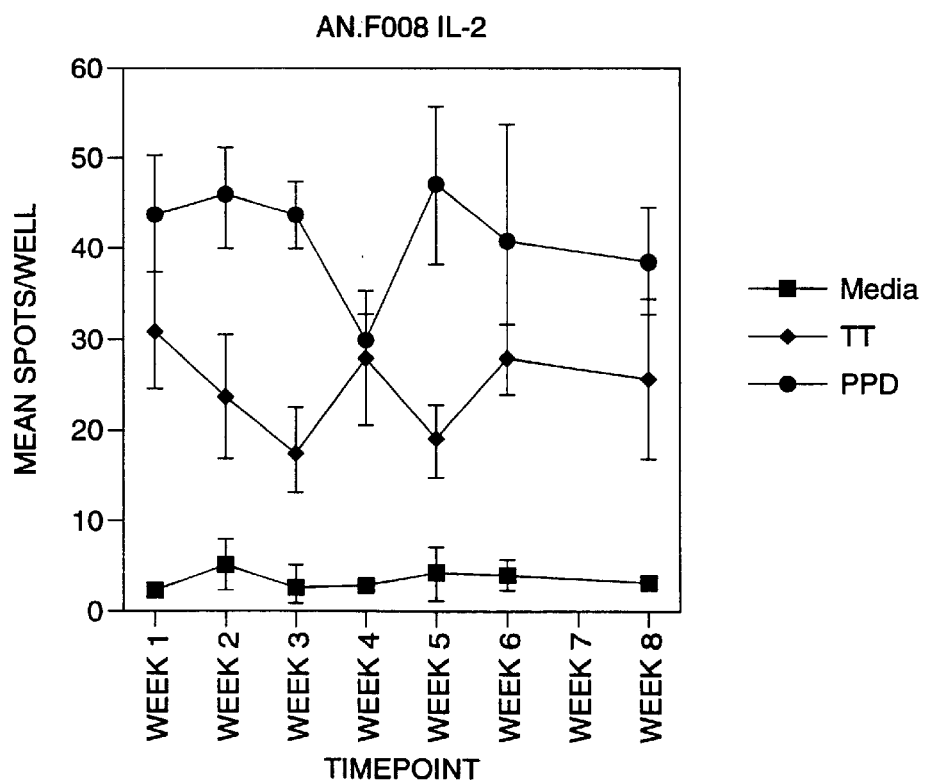
Figure 6A:
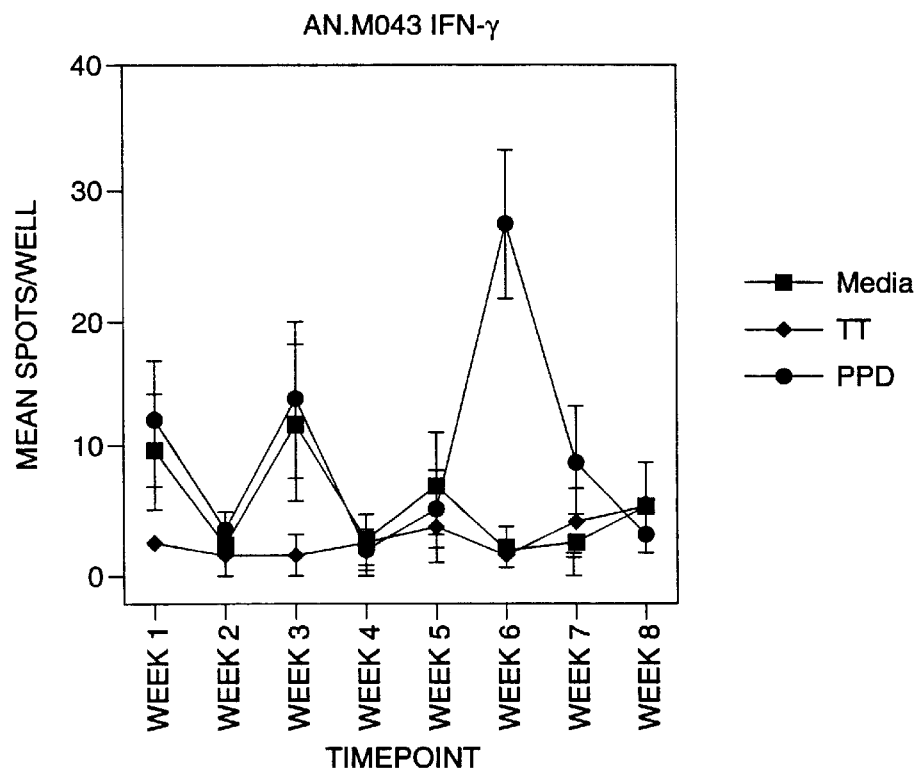
FIGS. 6A and 6B show T cell reactivity over time measured using INF-γ and IL-2 capture for Donor AN.M043
Figure 6B:
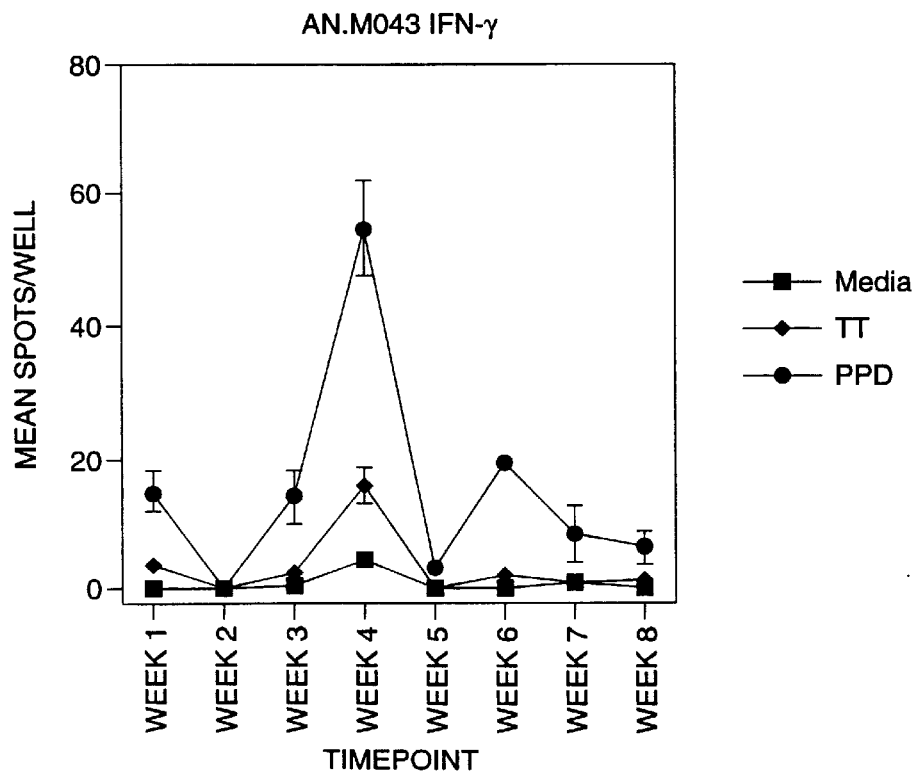

The measurement of antigen reactive T cells by IL-2 capture is illustrated in FIGS. 5 and 6. T cell reactivity over time was measured using both INF-γ and IL-2 capture. In carrying out these studies normal donors were drawn once a week on the same day of the week for eight weeks. PBMCs were purified by Ficoll™ gradient centrifugation and cryopreserved. Cells were thawed after collection of all samples and run in the RECALL ELISPOT for evaluation of TT and PPD responses. IFN-γ (FIG. 5A) and IL-2 (FIG. 5B) secreting cells were measured. Donor AN.F008 showed very stable reactivity to both antigens over the course of the study and for each lymphokine. Many, but not all, donors demonstrated similar stable responses to these two antigens. While the numbers of spots/well are similar for the IFN-γ and IL-2 responses for this donor, spot numbers usually vary between the lymphokines for a given antigen.

Donor AN.M043 (FIG. 6) displays a spike in reactivity to PPD during the course of the study. While the spike occurs in both lymphokine profiles, the spike does not occur at the same time, coming earlier in the IL-2 profile (week 4) than in the IFN-g profile (week 6). Repeat ELISPOTs on the same samples confirm the results.

EXPERIMENT III

Comparison of 3 and 10 Day Elispot Formats

Figures 7, 8:
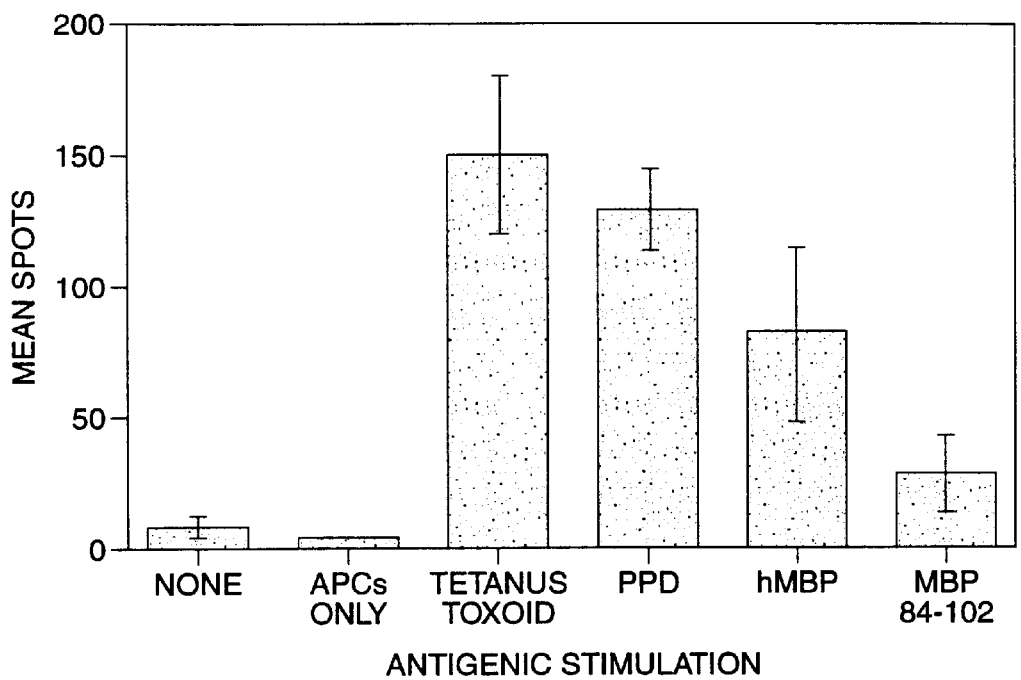
FIG. 7 shows IFN-γ produced by multiple sclerosis PBMCs following secondary stimulation by selected antigens
FIG. 8 shows comparison of IFN-γ spots obtained in the 3 day and 10 day assay formats. Antigens: TT, PPD, autoantigen (MBP, MBP 84-102).

The 10 day ELISPOT assay was used to identify patients with reactivity to the immunodominant peptide MBP 84-102. The assay was used for two phases of an MS clinical trial, patient recruitment and monitoring of the T cell response during the trial. As discussed supra, in the standard ELISPOT assay reported in the literature, PBMCs are mixed with antigen in a capture plate containing anti-lymphokine antibody for 1–2 days followed by detection with an enzyme-linked second antibody (3 day format). This assay tests $2 \times 10^5$ PBMCs per well, and because the frequency of autoreactive T cells in peripheral blood is on average in the range of $1–5/10^5$ there are very few specific cells per is well that can respond in the average patient. To increase the number of responders, the PBMCs were subjected to a round of ex vivo antigen stimulation prior to testing the recall response by lymphokine secretion. In other words, PBMCs were incubated with antigen or medium for 8 days, washed, restimulated with fresh irradiated APCs and antigen, and these restimulated cells were tested for secretion of IFN-γ by the capture ELISPOT (10 day format). Pooling all of the expanded cells from sextuplet wells and realiquoting them on day 9 into the capture plate improves the standard deviations. Table 3 shows a comparison of the two assay formats with blood from the same patient. The day 3 format gives a very low background, and the response to TT is measurable, averaging 36.7±15.3 IFN-γ spots for patient MS.M027. However, the response to whole human MBP and to the immunodominant peptide MBP 84-102 was nearly background and too low for effective statistical analysis. In contrast, a 7 day expansion before assay of lymphokine secretion yielded a higher background (25.0±1.4) but also a measurable improvement in the response to hMBP and to MBP 84-102. The response to TT was also increased in the 10 day format, with an average of nearly 100 spots per well. This density of response approaches the resolution limits of the video camera and software, reflecting the higher frequency of TT-reactive T cells in peripheral blood. For many patients and healthy controls the response to TT and/or to PPD is off scale in this 10 day format. However, it is expected that dilutions may be used which will keep the 10 day recall response to this antigens within measurable limits. As can be seen in FIGS. 7 and 8, many patients have strong responses to hMBP and/or MBP 84-102, as well as recall antigens such as TT and PPD, which can be compared with medium controls by Mann-Whitney analysis.

TABLE 3

Sample MS patient responses to antigens and medium in the
3 day and 10 day ELISPOT assay formats

| PATIENT | FORMAT | MEDIUM | TT | hMBP | MBP 84-102 |
|---|---|---|---|---|---|
| MS.M027 | 3 d assay | 0 ± 0 | 37 ± 15 | 1 ± 1 | 1 ± 1 |
|  | 10 d assay | 25 ± 1 | 99 ± 19 | 56 ± 31 | 63 ± 16 |
| MS.F134 | 10 d assay | 17 ± 3 |  | 36 ± 5 | 27 ± 7 |

The data in Table 4 illustrate the improved sensitivity of the "RECALL ELISPOT" assay compared to the standard ELISPOT. Blood from 21 RA patients were tested in the ELISPOT (standard and recall) to evaluate the reactivity to TT and PPD in the different formats. Patients were on standard medications for RA at the time of the draw including MAX., prednisone and various NSAIDS. Significant improvements in the ability to detect reactivity to TT and PPD were seen and approach levels of reactivity to these antigens seen in normal donors (~70%).

TABLE 4

|  | 3 DAY STANDARD ELISPOT ASSAY | | | 10 DAY RECALL ELISPOT ASSAY | | |
|---|---|---|---|---|---|---|
| PATIENT # | MEDIA | TT | PPD | MEDIA | TT | PPD |
| F200 |  |  |  | 0.3 ± 0.5 | 5.0 ± 2.4 | 3.7 ± 1.8 |
| F201 | 4.7 ± 3.4 | 7.8 ± 3.8 | 4.1 ± 2.6 | 0.7 ± 0.5 | 2.7 ± 1.0 | 7.2 ± 2.1 |
| F204 |  |  |  | 2.8 ± 1.7 | 6.5 ± 4.7 | 10.2 ± 2.3 |
| F500 | 0.8 ± 1.0 | 0.5 ± 1.2 | 2.7 ± 2.4 | 4.0 ± 2.1 | 8.0 ± 3.4 | TMTC |
| F501 |  |  |  | 1.7 ± 1.9 | 2.8 ± 3.0 | 9.5 ± 3.4 |
| M503 | 1.3 ± 1.0 | 3.5 ± 3.3 | 2.3 ± 2.0 |  |  |  |
| M504 | 3.3 ± 3.7 | 4.8 ± 4.1 | 2.5 ± 1.6 | 3.0 ± 1.3 | 38.2 ± 12.1 | 13.8 ± 2.3 |
| F505 | 2.5 ± 1.4 | 2.5 ± 1.6 | 4.0 ± 3.2 | 5.7 ± 2.2 | 15.7 ± 5.0 | 23.3 ± 2.7 |
| F506 | 11.3 ± 5.3 | 35.1 ± 7.4 | 8.7 ± 5.3 |  |  |  |
| F507 | 5.4 ± 2.9 | 20.0 ± 8.0 | 16.6 ± 3.9 |  |  |  |
| F508 | 3.3 ± 2.0 | 3.7 ± 2.2 | 2.1 ± 1.4 |  |  |  |
| M509 | 5.1 ± 3.9 | 3.4 ± 2.1 | 4.4 ± 2.9 | 2.5 ± 1.0 | 5.5 ± 2.6 | 5.0 ± 1.3 |
| M510 | 5.0 ± 2.1 | 9.3 ± 3.9 | 5.7 ± 2.4 |  |  |  |
| F511 | 3.4 ± 1.5 | 5.8 ± 3.2 | 5.3 ± 3.3 |  |  |  |
| F512 | 1.4 ± 1.9 | 6.0 ± 4.2 | 6.1 ± 5.8 | 5.0 ± 2.4 | 80.8 ± 12.3 | 37.0 ± 21.0 |
| F513 | 1.6 ± 1.3 | 7.7 ± 4.6 | 1.4 ± 1.8 |  |  |  |
| F514 |  |  |  | 1.5 ± 1.4 | 20.5 ± 6.0 | 38.2 ± 10.9 |
| F515 |  |  |  | 13.3 ± 2.4 | 82.5 ± 16.5 |  |
| F516 |  |  |  | 8.8 ± 3.0 | 109.3 ± 24.2 | 107.3 ± 26.4 |
| M518 |  |  |  | 0.5 ± 0.5 | 29.7 ± 10.7 | 14.3 ± 4.6 |
| M519 |  |  |  | 49.0 ± 14.6 | 23.2 ± 5.1 | 63.5 ± 24.5 |
| % POSITIVE |  | 15.4 | 7.7 |  | 50.0 | 71.4 |

TMTC = Too Many To Count
Boldface type indicates samples which are statistically significant at p ≤ 0.05.

EXAMPLE IV

Comparison of Fresh Vs. Frozen PBMCs in a 10 Day Elispot Assay

The objective of these experiments was to determine if reactivity to antigens was comparable and consistent between fresh PBMCs isolated from MS patient whole blood and frozen cells from the same patient. If so, frozen cells could provide an internal control with future bleeds from patients during clinical trials. The assay was done as described above using on day 1 either fresh PBMCs or frozen PBMCs which were thawed before use in the assay.

The first experiment was run using patient frozen cells to see if reactivity could be detected. In the first experiment, it can be seen from the two runs with MS patients (MS.F165 and MS.M122) that, in addition to a positive TT response, an MBP response is present (Tables 5 and 6).

TABLE 5

Results of frozen experiment with patient MS.F165.
Numbers represent mean spots from plate counted using NIH Image.

| Frozen PBMC's | Media | Tet. Tox. | whle. hMBP | MBP84-102 |
|---|---|---|---|---|
| Mean | 6 | 65 | 16 | 7 |
| Std. Dev. | 2 | 12 | 3 | 4 |

TABLE 6

Results of fresh vs. frozen experiment with patient MS.M122.
Numbers represent mean spots from plate counted using NIH Image 1.58.

| PBMC's | Media | Tet. Tox. | whle. hMBP | MBP84-102 |
|---|---|---|---|---|
| Fresh | 44 | 69 | 31 | 40 |
| Std. Dev. | 29 | 19 | 10 | 20 |
| Frozen | 10 | 120 | 45 | 33 |
| Std. Dev. | 5 | 23 | 21 | 10 |

The results showed that frozen PBMCs can be used in a complete ELISPOT assay and produce positive results in the form of spots.

Figure 9:
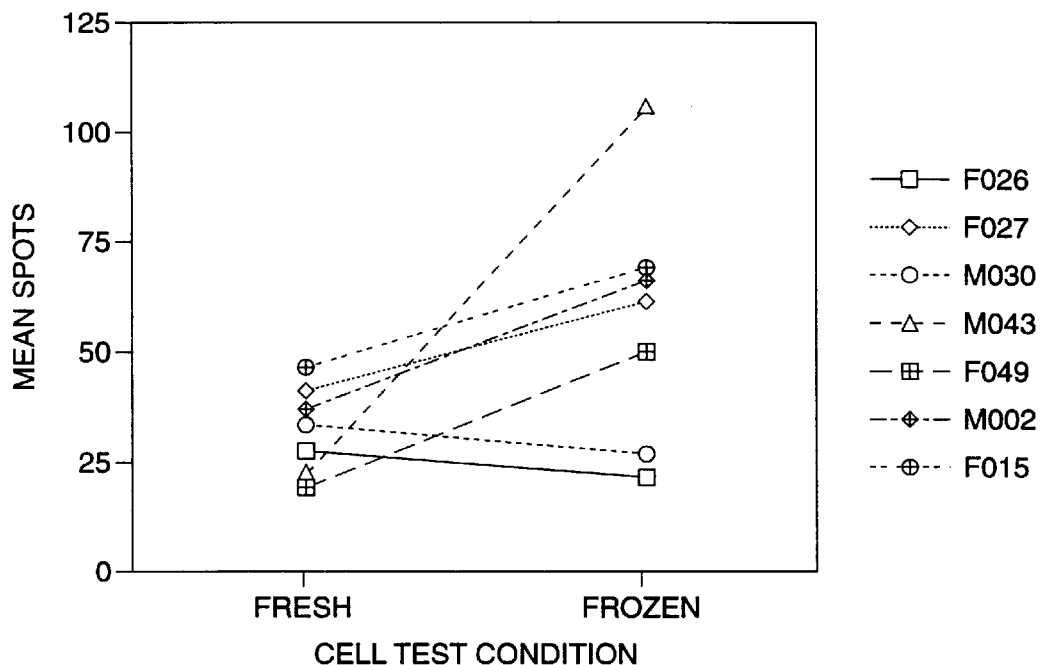
FIG. 9 shows the comparison between two experiments done on freshly isolated and frozen PBMCs thawed and then run on a 10 day ELISPOT assay. The cells are derived from healthy donors.

In the second experiment, shown in FIG. 9, seven healthy donors were evaluated for their TT response in the assay.

Statistically significant responses to TT were found in all seven donors. Responses from frozen cells were equivalent to or better than those obtained from fresh cells. This improved background to signal ratio was also seen in MS.M122 (Table 6). A possible explanation is the elimination of inhibitory cryosensitive cells (e.g., platelets).

Figure 10:
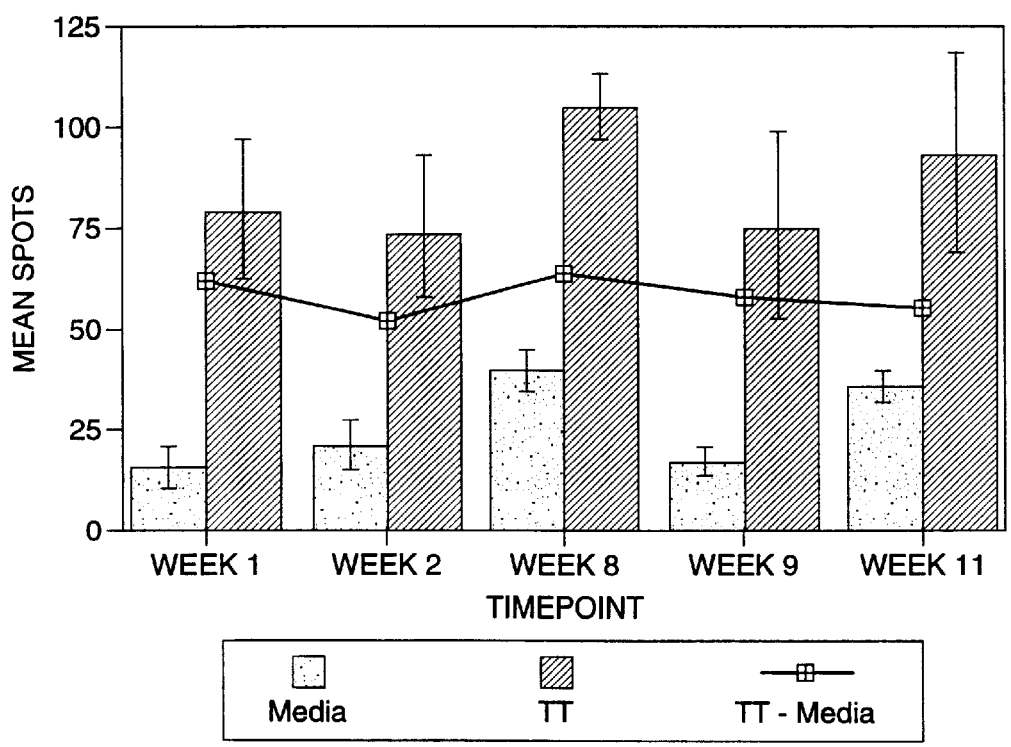
FIG. 10 shows the use of frozen PBMCs as a source of T cells and its utility as a reproducible internal control for the assay.

The third experiment looked at the response of the frozen cells of a known TT positive in-house donor, AN.M036. Frozen cells were derived from a unit of donated blood which was processed and frozen on the day of the unit draw collection, and stored in liquid nitrogen. Aliquots of the cells were thawed at various time intervals and run in the assay as described above. Timepoints shown were done by three different technicians. FIG. 10 shows the stability/reproducibility of the response over an 11 week period. This stability/reproducibility allows for the use of such cells as an internal control for the assay.

The stability of frozen PBMCs has several important implications. Because the response of frozen PBMCs is comparable to or better than the response measured in fresh PBMCs, samples can be safely frozen for assay at a convenient time. Furthermore, the reproducibility of the samples from week to week show that samples can be re-run to confirm prior results. The stability of the frozen samples also permits the collection of samples over time for simultaneous assay at the end of a study. This has proven particularly useful in clinical trial applications and where many samples are collected on a given day. Alteratively, if samples are assayed on different days the possibility of assay variation can be monitored by the inclusion of an internal standard. For example, blood may be collected from donors (e.g., healthy donors) whose frozen PBMCs give an optimal number of SFCs (generally 20–60) in response to an antigen (e.g., TT or PD) in the 10 day recall ELISPOT. Aliquots of the same draw can then be included on plates assayed on different days as an internal control for possible variations due to reagents, timing, or personnel.

EXAMPLE V

Kinetics of Lymphokine Capture and IL-2 Addition

Figure 11:
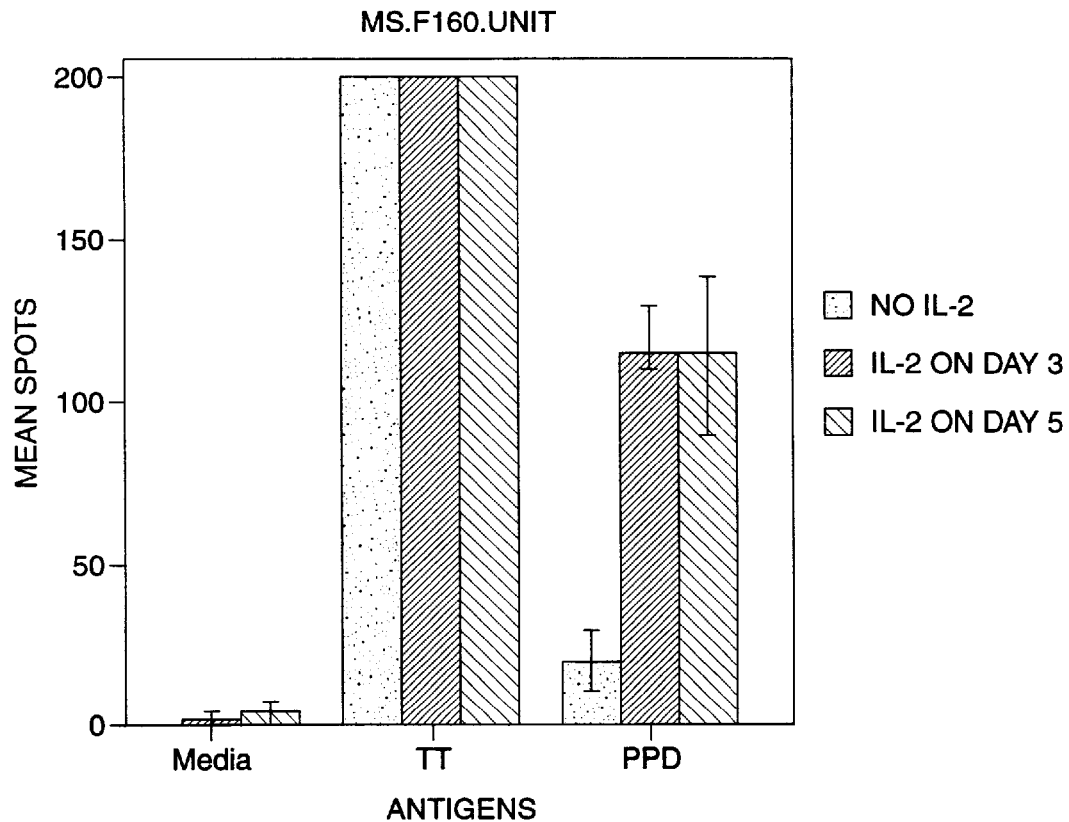
FIG. 11 shows the effects of IL-2 addition on assay days 3 and 5.

In this experiment the timing of addition of exogenous IL-2 addition to $T_h1$ cells was investigated. Addition of IL-2 several days after antigenic stimulation is often desirable when the antigen specific T cell frequency is low. FIG. 11 shows an example of the effect of exogenous IL-2 on the number of SFCs in a 10 day RECALL ELISPOT of an MS patient's response to TT and PPD. PBMCs were plated at $2 \times 10^5$ cells/well and stimulated with either Tetanus Toxoid (TT at 50 µg/ml), PPD (50 µg/ml), or media as a control. Quadruplicates for each antigen group were given 10 units/ml of IL-2 either on day 3, day 5, or no IL-2 at all. A previous 3 day ELISPOT of this patient showed a relatively high response to TT and few cells responding to PPD (data not shown). In the 10 day recall ELISPOT, addition of IL-2 on day 3 or day 5 raised the level of background SFCs very slightly, but significantly improved the number of SFCs responding to PPD. In contrast, the recall response to TT was so high that an effect by IL-2 could not be measured. There may be a threshold responder frequency above which the cells are able to supply sufficient IL-2 to drive optimal autocrine growth. Clearly the number of SFCs is enhanced by exogenous IL-2 when the frequency of these cells is low, and addition of IL-2 on day 3 or day 5 is equally effective.

EXAMPLE VI

Generation of T Cell Clones

Figure 12:
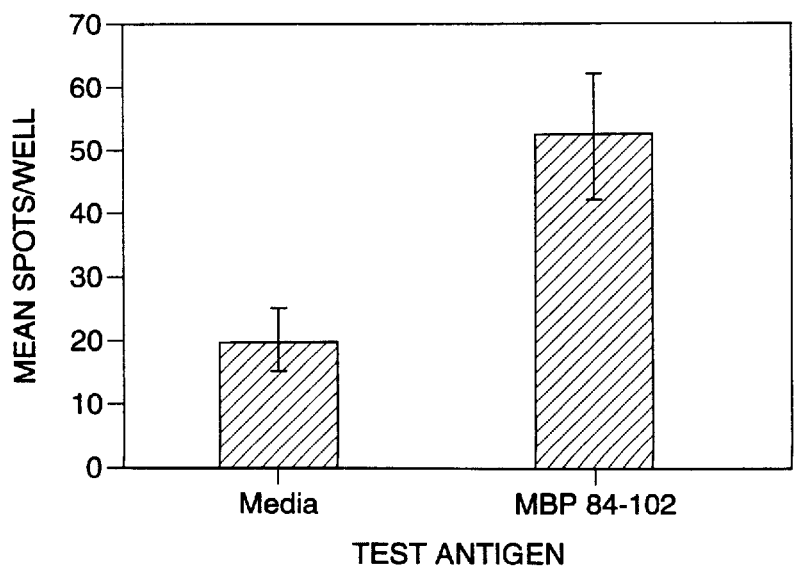
FIG. 12 shows the use of the Recall Elispot in cloning.

This example demonstrates the use of the RECALL ELISPOT in cloning. To increase the chances of successful cloning of MBP 84-102, DR2 restricted T cell clones, three screening criteria were established. 1) Donors had to satisfy blood bank qualifications for unit donations. This would ensure sufficient quantities of blood to carry out the cloning procedures. 2) Donors had to be DRb1*1501 and DRb5*0101. HLA typing was preformed by Cross Clinical Laboratories (Kansas City, Mo.). 3) Donors had to demonstrate positive T cell reactivity to MBP 84-102 in the RECALL ELISPOT assay. This would ensure that cells capable of recognizing the peptide of interest are present, though not necessarily being recognized in the correct DR context. Patient MS.F132 fulfilled these requirements and was used for the cloning project (Table 7). This patient had relapsing progressive MS with exacerbation in January of Year 2 of the study. FIG. 12 shows the RECALL ELISPOT of the "June 20" draw from Table 7.

TABLE 7

Patient MS.F132

| PATIENT # | DR TYPE | TEST DATE | MBP REACTIVITY | MBP 84-102 REACTIVITY |
| --- | --- | --- | --- | --- |
| MS.F132 | 2, 3 | Year 1, Oct. 18 | + | − |
|  |  | Year 2, Feb 7 | + | + |
|  |  | Year 2, June 20 | ND | + |

Use of the cloning criteria described supra resulted in the successful cloning of MBP 84-102 specific, DR2 restricted T cells with 6 of 300 wells positive for reactivity to MBP (Table 8) Insufficient expansion of clones D5, D9 and F9 led to freezing for further characterization at a later time. Of the three clones (D3, E6 and E11) which expanded sufficiently to characterize, ⅔ (66%) were DR2 restricted and MBP 84-102 reactive. Given that MBP 84-102 is the immunodominant epitope of DR2 and that none of the tested overlapping MBP peptides bind to DR3 (Valli et al., 1993, J. Clin. Invest. 91:616), the three uncharacterized clones also have a good chance of fulfilling the cloning goal.

TABLE 8

Use of the RECALL ELISPOT in Cloning

| Clone | SI at First Screening | MBP Reactive | MBP 84-102 Reactive | DR2 Restricted |
| --- | --- | --- | --- | --- |
| D3 | 2 | + | − | − |
| D5 | 2 | + | ND | ND |
| D9 | 2 | + | ND | ND |
| E6 | 4 | + | + | + |
| E11 | 2 | + | + | + |
| F9 | 3 | + | ND | ND |

EXAMPLE VII

Epitope Identification

Figure 13:
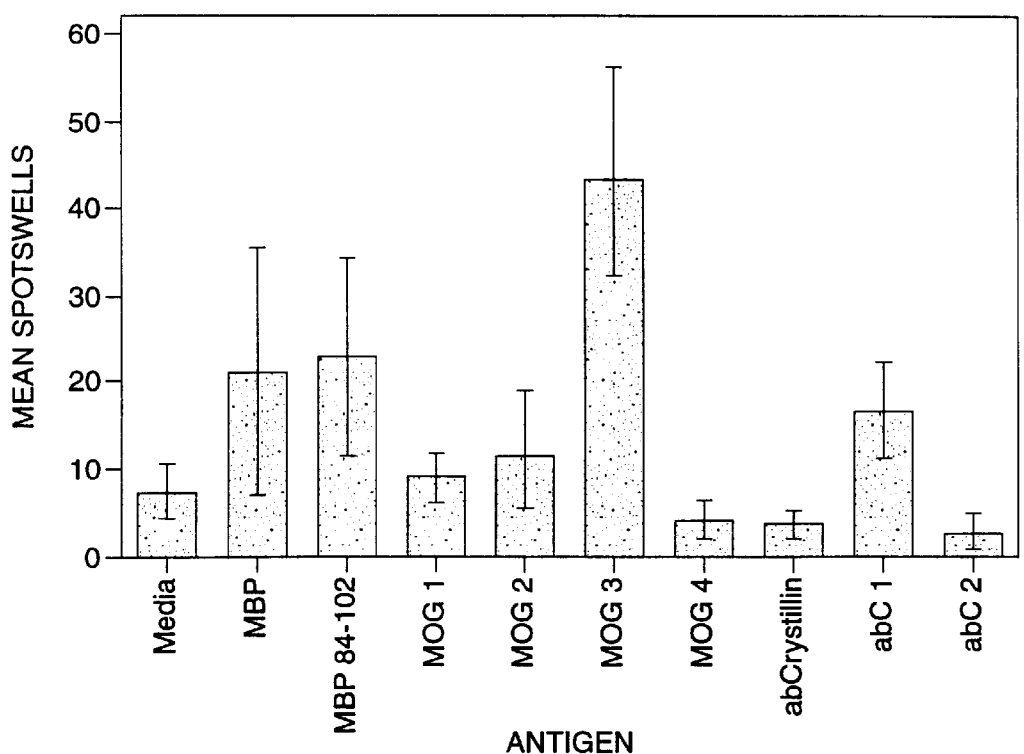
FIG. 13 shows the use of the Recall Elispot in epitope identification.

The RECALL ELISPOT assay can be used for epitope identification, as illustrated in FIG. 13. 45 ml of peripheral blood from an MS patient was run in the RECALL ELISPOT to evaluate reactivity to various myelin associated proteins and peptides. Statistically significant responses ($p \leq 0.05$) are marked (*). RECALL ELISPOT allows the rapid screening of large numbers of patients and antigens using a small amount of blood.

EXAMPLE VIII

Figure 14:
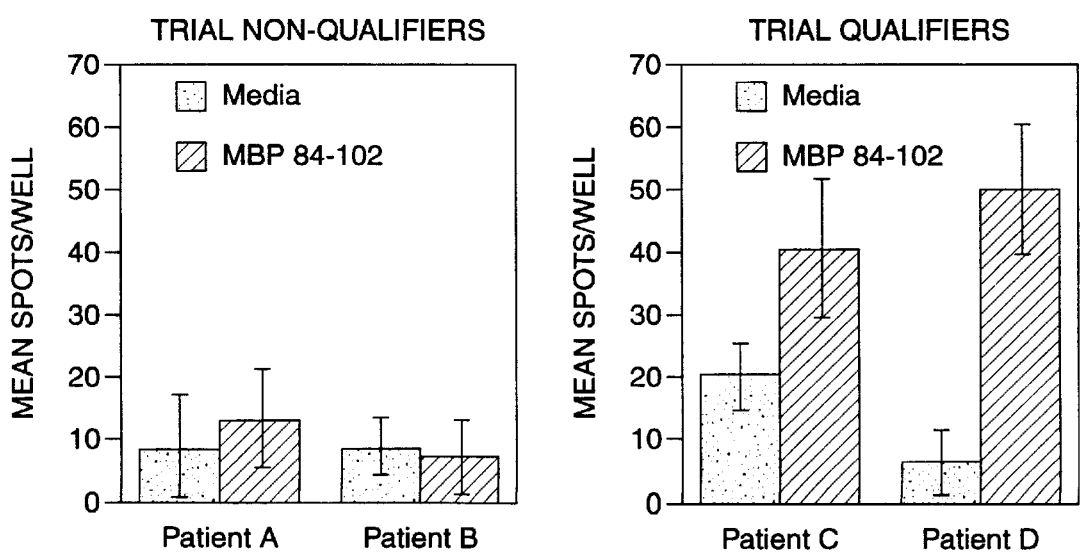
FIG. 14 shows identification of patient reactivity for antigen-specific clinical trials.

Identification of Patients Who Exhibit a T Cell Response to a Peptide of Interest The RECALL ELISPOT assay can be used to identify patients who are reactive to the antigen of interest for inclusion in clinical trials. The results of four inclusion ELISPOTs for an MS trial are shown (FIG. 14) where inclusion requires that MBP 84-102 reactivity be greater than media at a p value of $\leq 0.05$.

EXAMPLE IX

Figure 15A:
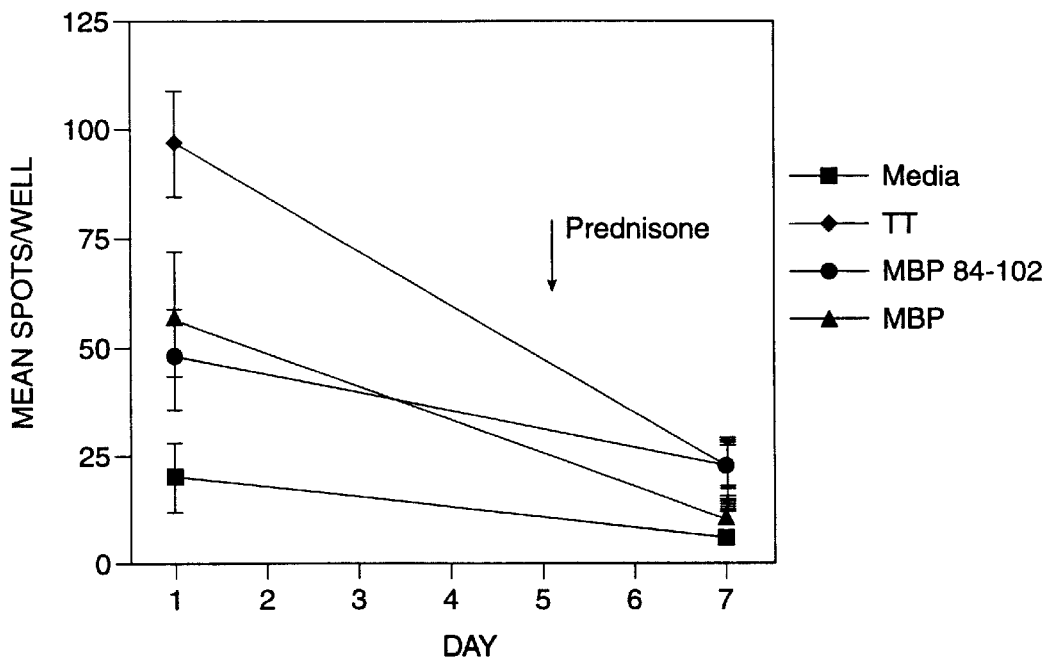
FIGS. 15A and 15B show monitoring of recall antigen responses to look at generalized immunosuppression.

Monitoring Antigen Reactivity Following Administration of Immunosuppressive and Putatively Immunosuppressive Drugs A normal donor with known consistent positive reactivity to TT, MBP and MBP 84-102 had blood drawn on DAY 1 for a recall ELISPOT. On DAY 5 the donor was placed on high dose prednisone for treatment of a rash. An ELISPOT of blood drawn two days later (DAY 7) showed the dramatic reduction in reactivity to all three antigens, with reactivity to MBP becoming statistically non-significant (FIG. 15A). These results illustrate the use of the RECALL ELISPOT assay for assaying the effects of an immunosuppressive treatment.

Figure 15B:
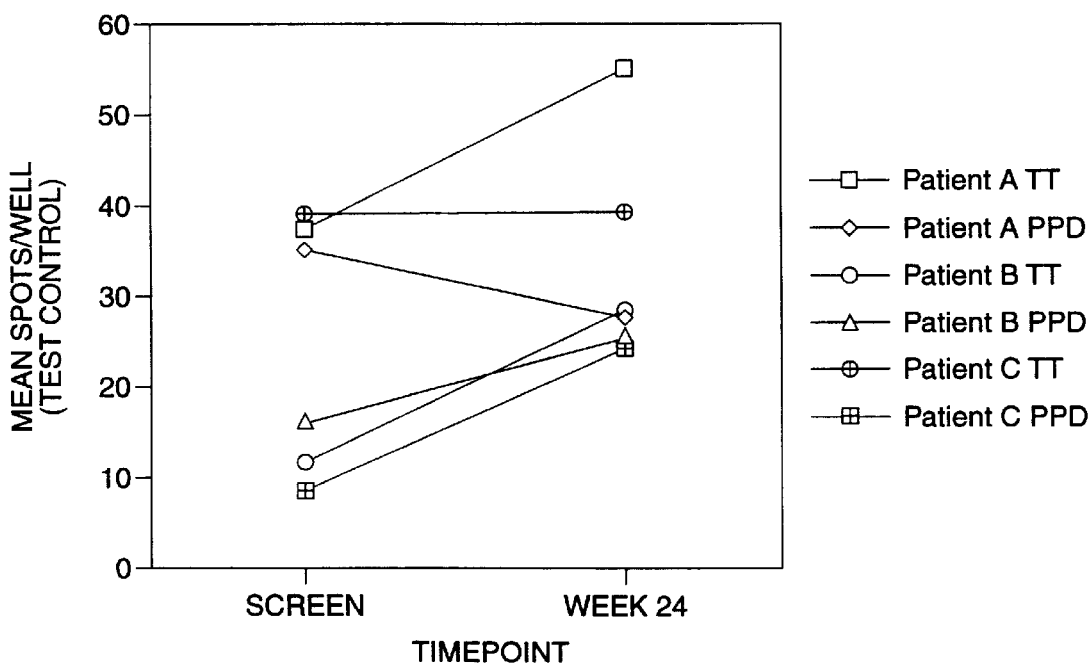

FIG. 15B shows results from TT and PPD ELISPOT assays of three patients enrolled in a clinical trial of a drug with possible immunosuppressive effects. Patients received multiple doses of drug during the 24 week period shown and a TT booster (wk 6–8). All patients began with statistically significant ($p \geq 0.05$) reactivities and maintained those reactivities at the end of the 24 weeks.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method for detecting an antigen reactive human T-cell in a biological sample suspected of containing said T-cells, the method comprising:
   (a) stimulating the T-cells in the biological sample with an antigen comprising a T cell epitope for a first time period sufficient to permit T-cell expansion;
   (b) restimulating the T-cells with an effective amount of a combination of an antigen comprising the T cell epitope and antigen presenting cells for a second time period effective to induce secretion of a soluble factor;
   (c) detecting the presence of the soluble factor by capturing the soluble factor on a solid support; and
   (d) relating the presence of the soluble factor on the solid support to the presence of the antigen reactive T-cell.

2. The method of claim 1, wherein the biological sample is cerebrospinal fluid or synovial fluid.

3. The method of claim 1, wherein the soluble factor is a lymphokine.

4. The method of claim 3, wherein the soluble factor is IL-5 or RANTES.

5. The method of claim 1, wherein the soluble factor is captured in step (c) by being bound to an antibody immobilized on the solid support.

6. The method of claim 5, wherein the solid support is a plastic support.

7. The method of claim 6, wherein the solid support is a polyvinyl difluoride (PVDF).

8. The method of claim 3, wherein the antigen presenting cells in step (b) are B cells, macrophages and/or dendritic cells.

9. The method of claim 8, wherein the antigen presenting cells are from blood.

10. The method of claim 8, wherein the antigen presenting cells are dendritic cells that have been expanded in culture.

11. The method of claim 1, wherein at least one cytokine, growth factor or combination thereof, is added during or after step (a) to facilitate continued T-cell expansion.

12. The method of claim 11, wherein IL-2, IL-4, and/or IL-2 is added.

13. The method of claim 11, wherein more than one cytokine is added.

14. The method of claim 13, wherein said more than one cytokines are from mitogen stimulated T lymphocytes.

15. The method of claim 1, wherein at least two different soluble factors are detected.

16. The method of claim 15, wherein the different soluble factors are secreted by the same cell type in the sample.

17. The method of claim 15, wherein at least one soluble factor from a $T_h 1$ cell factor and at least one soluble factor is from a $T_h 2$ cell.

18. A method of periodically monitoring levels of antigen reactive T-cells in a patient comprising:
   (a) providing a sample of PBMCs from the patient;
   (b) freezing a portion of the sample of PBMCs to provide a control sample;
   (c) assaying the level of antigen reactive T-cells in the patient at periodic intervals using the assay of claim 1, wherein the intervals are of equal duration;
   (d) assaying the level of antigen reactive T-cells in a freshly thawed portion of the control sample using the assay of claim 1; and
   (e) comparing the levels observed in (c) and (d) to monitor the levels of antigen reactive T-cells in the patient.

19. A method of periodically monitoring levels of antigen reactive T-cells in a patient comprising:
   (a) providing a sample of PBMCs from the patient;
   (b) freezing a portion of the sample of PBMCs to provide a control sample;
   (c) assaying the level of antigen reactive T-cells in the patient at least twice at periodic intervals using the assay of claim 1;
   (d) assaying the level of antigen reactive T-cells in a freshly thawed portion of the control sample using the assay of claim 1; and
   (e) comparing the levels observed in (c) and (d) to monitor the levels of antigen reactive T-cells in the patient, wherein a drug or treatment is administered to the patient between two assays of step (c).

20. A method of monitoring levels of antigen reactive T-cells in a patient comprising:
   (a) collecting and freezing samples of PBMCs from the patient at least two different times; and (b) thawing the samples and assaying the level of antigen reactive T-cells in the samples using the assay of claim 1.

21. The method of claim 20 wherein a drug or treatment is administered to the patient between the two collections of step (a).

22. A method of determining the effect of a drug or treatment on levels of antigen reactive T-cells in a patient comprising:
   (a) assaying the level of antigen reactive T-cells in the patient a first time using the assay of claim 1;
   (b) administering the drug or treatment to the patient;
   (c) assaying the level of antigen reactive T-cells in the patient a second time using the assay of claim 1;
   (d) comparing the levels observed in (a) and (c) to determine the effect of the drug or treatment on levels of antigen reactive T-cells in the patient.

23. The method of claim 22 wherein the assay of the level of antigen reactive T-cells in the patient before administration of the drug or treatment is carried out at least twice.

24. The method of claim 23 wherein the wherein the assay of the level of antigen reactive T-cells in the patient after administration of the drug or treatment is carried out at least twice.

25. The method of claim 22 wherein the drug or treatment is immunosuppressive.

26. A method for identifying an immunodominant T cell eptiope associated with a disease, condition or symptom, comprising:
   (a) determining the reactivity of T cells from a first plurality of individuals to a peptide comprising a T cell epitope, wherein said individuals are diagnosed with a the disease or symptom, wherein said determining comprises a step of restimulation with the peptide;
   (b) determining the reactivity of T cells from a second plurality of individuals to the peptide, wherein said individuals are not diagnosed with the disease or symptom, wherein said determining comprises a step of restimulation with the peptide comprising a T cell epitope;
   (c) comparing the reactivity of T cells from the first plurality of individuals to the reactivity of T cells from the second plurality of individuals; and,
   (d) correlating an increased level of reactivity to the peptide in first plurality of individuals compared to the second plurality of individuals with the presence in the peptide of a T cell epitope associated with the disease or symptom,
   wherein the step of determining the reactivity to the peptide in steps (a) and (b) is carried out using the assay of claim 1.

27. The method of claim 26, wherein the disease, condition or symptom is an autoimmune disease.

28. The method of claim 27, wherein the autoimmune disease is multiple sclerosis, diabetes, myasthenia gravis or rheumatoid arthritis.

29. The method of claim 26, wherein the peptide is a fragment of a known or suspected autoantigen protein.

30. The method of claim 1, further comprising detecting an immunoglobulin secreted by a B cell in the biological sample.

31. The method of claim 30, wherein the immunoglobulin is an anti-myelin protein antibody.

32. The method of claim 31, wherein the immunoglobulin is an IgG.

* * * * *